US011440970B2

(12) United States Patent
Kalnik et al.

(10) Patent No.: US 11,440,970 B2
(45) Date of Patent: Sep. 13, 2022

(54) NICOTINE-BINDING ANTIBODIES

(71) Applicants: ANTIDOTE THERAPEUTICS, INC., Bethesda, MD (US); BliNK BIOMEDICAL, Marseilles (FR); Hennepin Healthcare Research Institute, Minneapolis, MN (US)

(72) Inventors: Matthew W. Kalnik, Gaithersburg, MD (US); Thomas Thisted, Gaithersburg, MD (US); Nicola Beltraminelli, Marseilles (FR); Stéphanie Fallot, Marseilles (FR); Zuzana Biesova, Bethesda, MD (US); Steve Fuller, Bethesda, MD (US); Mark G. Lesage, Minneapolis, MN (US); Paul Pentel, Minneapolis, MN (US)

(73) Assignees: ANTIDOTE THERAPEUTICS, INC., Bethesda, MD (US); BliNK BIOMEDICAL, Marseilles (FR); Hennepin Healthcare Research Institute, Minneapolis, MN (US)

( * ) Notice: Subject to any disclaimer, the term of this patent is extended or adjusted under 35 U.S.C. 154(b) by 383 days.

(21) Appl. No.: 16/639,050

(22) PCT Filed: Aug. 14, 2018

(86) PCT No.: PCT/US2018/046621
§ 371 (c)(1),
(2) Date: Feb. 13, 2020

(87) PCT Pub. No.: WO2019/036419
PCT Pub. Date: Feb. 21, 2019

(65) Prior Publication Data
US 2020/0377616 A1 Dec. 3, 2020

Related U.S. Application Data

(60) Provisional application No. 62/545,696, filed on Aug. 15, 2017.

(51) Int. Cl.
*C07K 16/44* (2006.01)
*A61K 47/60* (2017.01)
*A61P 25/34* (2006.01)
*A61K 9/00* (2006.01)

(52) U.S. Cl.
CPC ............ *C07K 16/44* (2013.01); *A61K 9/0019* (2013.01); *A61K 47/60* (2017.08); *A61P 25/34* (2018.01)

(58) Field of Classification Search
None
See application file for complete search history.

(56) References Cited

U.S. PATENT DOCUMENTS

| | | |
|---|---|---|
| 6,232,082 B1 | 5/2001 | Ennifar et al. |
| 7,446,205 B2 | 11/2008 | Ennifar |
| 7,547,712 B2 | 6/2009 | Ennifar et al. |
| 8,232,072 B2 | 7/2012 | Kalnik et al. |
| 8,344,111 B2 | 1/2013 | Bachmann et al. |
| 2003/0118592 A1 | 6/2003 | Ledbetter et al. |
| 2003/0133939 A1 | 7/2003 | Ledbetter et al. |
| 2006/0111271 A1 | 5/2006 | Cerny et al. |
| 2014/0056879 A1 | 2/2014 | Lazar |

FOREIGN PATENT DOCUMENTS

| | | |
|---|---|---|
| EP | 0 194 158 A2 | 9/1986 |
| WO | WO-00/32239 A1 | 6/2000 |
| WO | WO-02/058635 A2 | 8/2002 |
| WO | WO-03/082329 A2 | 10/2003 |
| WO | WO-2009/068335 A1 | 6/2009 |

OTHER PUBLICATIONS

Chen "Enhancement and destruction of antibody function by somatic mutation: unequal occurrence is controlled by V gene combinatorial associations" EMBO 14(12):2784-2794 1995 (Year: 1995).*
Carrera et al., "Investigations using immunization to attenuate the psychoactive effects of nicotine," Bioorg med Chem 12(3):563-0 (2004).
Dall'Acqua et al., "Properties of Human IgG1s Engineered for Enhanced Binding to the Neonatal Fc Receptor (FcRn)," J. Biol Chem., 281, No. 33, pp. 23514-23524 (Aug. 2006).
Keyler et al., "Monoclonal Nicotine-Specific Antibodies Reduce Nicotine Distribution to Brain in Rats: Dose- and Affinity-Response Relationships," Drug Metabolism and Disposition, Pharmacology and Experimental Therapeutics, vol. 33, No. 7, pp. 1056-1061 (Jul. 2005).
Labrijn et al., "Therapeutic IgG4 antibodies engages in Fab-arm exchange with endogenous human IgF4 in vivo," Nature Biotech 27(8): 767-71 (2009) (Published online Jul. 2009).
Pentel et al., "Differential Effects of Passive Immunization with Nicotine-Specific Antibodies on the Acute and Chronic Distribution of Nicotine to Brain in Rats," Journal of Pharmacology and Experimental Therapeutics, vol. 317, No. 2, pp. 660-666 (May 2006).
Rollema et al., "Pharmacological profile of the $\alpha_4 \beta_2$ nicotinic acetylcholine receptor partial agonist varenicline, an effective smoking cessation aid," Neuropharmacology, 52: 985-994 (2007).
Tars et al., "Different Binding Modes of Free and Carrier-Protein-Coupled Nicotine in a Human Monoclonal Antibody," J. Mol. Bio., 415: 118-127 (2012).

* cited by examiner

*Primary Examiner* — Adam Weidner
(74) *Attorney, Agent, or Firm* — Foley & Lardner LLP

(57) ABSTRACT

Described are novel nicotine-binding antibodies and methods of using them for treating nicotine addiction and/or facilitating smoking cessation, or for treating nicotine overdose or nicotine poisoning.

18 Claims, 7 Drawing Sheets

Specification includes a Sequence Listing.

```
SEQUENCE LISTING

<160> NUMBER OF SEQ ID NOS: 40

<210> SEQ ID NO 1
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Gln Val Arg Leu Gln Glu Ser Gly Pro Gly Leu Val Lys Pro Ser Gly
1               5                   10                  15

Thr Leu Ser Leu Thr Cys Ala Val Ser Gly Gly Ser Ile Tyr Ser Ser
            20                  25                  30

Asn Trp Trp Thr Trp Val Arg Gln Pro Pro Gly Lys Gly Leu Glu Trp
        35                  40                  45

Val Gly Glu Ile His Ile Arg Gly Thr Thr Tyr Tyr Asn Pro Ser Leu
    50                  55                  60

Asn Ser Arg Val Thr Ile Ser Leu Asp Lys Ser Asn Asn Gln Val Ser
65                  70                  75                  80

Leu Arg Leu Thr Ser Val Thr Ala Ala Asp Ser Ala Val Tyr Tyr Cys
                85                  90                  95

Val Ser Gln Glu Val Gly Gly Pro Asp Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 2
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Asn Phe Met Leu Thr Gln Pro His Ser Val Ser Glu Ser Pro Gly Lys
1               5                   10                  15

Thr Val Thr Ile Ser Cys Thr Arg Ser Gly Gly Ser Ile Ala Thr Tyr
            20                  25                  30

Tyr Val Gln Trp Tyr Gln Arg Pro Gly Ser Ala Pro Thr Asn Val
        35                  40                  45

Ile Tyr Lys Tyr Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Asn
                85                  90                  95

Asn Ile Gln Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

```
Arg Ser Tyr Ser Cys Gln Val Thr His Glu Gly Ser Thr Val Glu Lys
            195                 200                 205

Thr Val Ala Pro Thr Glu Cys Ser
    210                 215

<210> SEQ ID NO 3
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gln Leu Gln Leu Gln Glu Ser Gly Pro Gly Leu Val Lys Pro Ser Glu
1               5                   10                  15

Thr Leu Ser Leu Ile Cys Thr Val Ser Gly Gly Ser Ile Arg Lys Asn
            20                  25                  30

Asn Glu Trp Trp Ala Trp Ile Arg Gln Ala Pro Gly Lys Gly Leu Glu
        35                  40                  45

Trp Ile Gly Ser Leu Ser Tyr Thr Gly Arg Thr Val Tyr Asn Pro Ser
50                  55                  60

Leu Lys Ser Arg Val Thr Ile Ser Thr Asp Thr Ser Glu Thr Gln Phe
65                  70                  75                  80

Ser Leu Lys Val Asn Ser Val Thr Ala Ala Asp Thr Ala Val Tyr Tyr
                85                  90                  95

Cys Ala Arg Leu Ser Pro Phe Val Gly Ala Ala Trp Trp Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
```

```
                    325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Asp Glu Leu Thr Lys Asn Gln
            355                 360                 365
Val Ser Leu Thr Cys Leu Val Lys Gly Phe Tyr Pro Ser Asp Ile Ala
        370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
Val Met His Glu Ala Leu His Asn His Tyr Thr Gln Lys Ser Leu Ser
            435                 440                 445
Leu Ser Pro Gly Lys
        450

<210> SEQ ID NO 4
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Glu Val Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Arg
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Ile Gly Thr Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Ala Tyr Ser Pro
                85                  90                  95
Pro Ala Ile Thr Phe Gly Gly Gly Thr Lys Val Glu Ile Lys Arg Thr
            100                 105                 110
Val Ala Ala Pro Ser Val Phe Ile Phe Pro Pro Ser Asp Glu Gln Leu
        115                 120                 125
Lys Ser Gly Thr Ala Ser Val Val Cys Leu Leu Asn Asn Phe Tyr Pro
    130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Val Tyr Ala Cys Glu Val Thr His Gln Gly Leu Ser Ser Pro Val
        195                 200                 205
Thr Lys Ser Phe Asn Arg Gly Glu Cys
    210                 215
```

<210> SEQ ID NO 5
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

```
Gln Leu Gln Leu Gln Glu Ser Gly Pro Gly Leu Leu Lys Pro Ser Glu
1               5                   10                  15

Thr Leu Ser Leu Thr Cys Thr Val Ser Gly Gly Ser Val Thr Thr Ser
            20                  25                  30

Pro Asp Trp Trp Ala Trp Leu Arg Gln Ser Pro Gly Lys Gly Leu Glu
        35                  40                  45

Trp Ile Gly Ser Val Ser Tyr Thr Gly Arg Thr Val Tyr Asn Pro Ser
    50                  55                  60

Leu Lys Ser Arg Val Thr Ile Ser Leu Asp Thr Ser Lys Asn His Leu
65                  70                  75                  80

Ser Leu Arg Met Thr Ser Ala Thr Ala Ala Asp Thr Ala Val Phe Tyr
                85                  90                  95

Cys Ala Arg Leu Thr Pro Ile Asp Arg Phe Ser Ala Asp Tyr Tyr Val
            100                 105                 110

Leu Asp Ile Trp Gly Gln Gly Ala Thr Val Thr Val Ser Ser Ala Ser
        115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350
```

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
435                 440                 445

Ser Leu Ser Leu Ser Pro Gly Lys
    450                 455

<210> SEQ ID NO 6
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 6

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Phe Gln His Lys Pro Gly Gln Ala Pro Arg Leu Leu Ile
        35                  40                  45

Phe Arg Ser Ser Thr Arg Ala Thr Gly Thr Pro Pro Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln His Tyr Ser Tyr Trp Pro Pro
                85                  90                  95

Leu Ile Thr Phe Gly Gln Gly Thr Arg Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 7
<211> LENGTH: 458
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Gln Leu Gln Leu Arg Glu Ser Gly Pro Gly Leu Val Lys Pro Ser Glu
1               5                   10                  15

Thr Leu Ser Leu Thr Cys Ser Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Thr Gly Arg Thr Tyr Tyr Asn Pro Ser
    50                  55                  60

Leu Glu Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Gly Leu His Tyr Ser Trp Ser Ala Leu Gly Gly Tyr Tyr Phe
            100                 105                 110

Tyr Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380
```

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
        420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 8
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Asp Leu Val Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Lys Tyr Gly Ser Ser Pro
                85                  90                  95

Pro Arg Ile Thr Phe Gly Pro Gly Thr Lys Val Asp Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 9
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

```
Gln Leu Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Ser Ser Ser
            20                  25                  30

Ser Tyr Tyr Trp Gly Trp Ser Arg Gln Ser Pro Gly Lys Gly Leu Glu
        35                  40                  45

Trp Ile Ala Ser Ile Tyr Tyr Ser Gly Ser Thr Tyr Tyr Asn Pro Ser
    50                  55                  60

Leu Lys Ser Arg Val Thr Ile Phe Ile Asp Thr Ser Lys Asn Gln Phe
65                  70                  75                  80

Ser Leu Lys Leu Ser Ser Val Thr Ala Ala Asp Thr Ala Ile Tyr Tyr
                85                  90                  95

Cys Ala Arg Val Gly Thr Ser Ala Met Ser Arg Ala Phe Asp Met Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
```

```
                    405                 410                 415
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 10
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Gln Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Lys Val Glu Ala Glu Asp Val Gly Val Tyr Phe Cys Met Gln Ala
                85                  90                  95

Leu Gln Ile Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 11
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser Arg Arg
            20                  25                  30

Asn Asp Tyr Trp Ala Trp Ile Arg Gln Ser Pro Gly Lys Asp Leu Glu
            35                  40                  45

Trp Ile Gly Thr Ile Ser Phe Ser Gly Ser Thr Phe Tyr Asn Pro Ser
 50                  55                  60

Leu Lys Ser Arg Val Thr Ile Ser Ala Asp Thr Phe Asn Asn His Phe
 65                  70                  75                  80

Ser Leu Arg Leu Asp Ala Val Ala Ala Asp Thr Ala Val Tyr Tyr
                85                  90                  95

Cys Ala Arg Leu Ser Pro Phe Val Gly Ala Ala Trp Trp Phe Asp Pro
            100                 105                 110

Trp Gly Pro Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430
```

Val Met His Glu Ala Leu His Asn His Tyr Thr Gln Lys Ser Leu Ser
        435                 440                 445

Leu Ser Pro Gly Lys
    450

<210> SEQ ID NO 12
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Ser Ser Asn
            20                  25                  30

Tyr Leu Gly Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Gly Val Tyr Tyr Cys Gln Arg Tyr Gly Arg Ser Pro
                85                  90                  95

Pro Ala Ile Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 13
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gln Leu Gln Leu Gln Glu Ser Gly Pro Gly Leu Val Lys Pro Ser Glu
1               5                   10                  15

Thr Leu Ser Leu Thr Cys Thr Ala Ser Gly Gly Ser Ile Thr Asn Asn
            20                  25                  30

Ile Asp Tyr Trp Val Trp Ile Arg Gln Pro Pro Gly Arg Gly Leu Glu

```
                    35                  40                  45
Trp Ile Gly Thr Ile Tyr Tyr Ser Gly Ser Thr Phe Tyr Asn Pro Ser
            50                  55                  60

Leu Lys Ser Arg Val Thr Ile Ser Val Asp Thr Ser Asn Asn Gln Phe
65                  70                  75                  80

Ser Leu Asn Leu Asn Ser Met Ser Ala Ala Asp Thr Ala Val Tyr Tyr
                85                  90                  95

Cys Ala Arg Leu Arg Tyr Tyr Asp Ser Asn Gly Tyr Leu Pro Tyr
            100                 105                 110

Trp Ile Asp Ser Trp Gly Gln Gly Thr Leu Val Thr Val Ser Ser Ala
            115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
            355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
450                 455
```

<210> SEQ ID NO 14
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Phe Cys Gln Leu Tyr Arg Arg Ser Pro
                85                  90                  95

Pro Arg Leu Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 15
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

```
Gln Leu Gln Leu Gln Glu Ser Gly Pro Gly Leu Val Lys Pro Ser Glu
1               5                   10                  15

Ser Leu Ser Leu Thr Cys Thr Val Ser Gly Gly Ser Ile Ile Ser Asn
            20                  25                  30

Asp Tyr Tyr Trp Ala Trp Ile Arg Gln Ser Pro Gly Lys Gly Leu Glu
        35                  40                  45

Trp Ile Gly Ser Ile Asn Tyr Arg Gly Ser Thr Phe Tyr Ser Pro Ser
    50                  55                  60
```

```
Leu Asn Ser Arg Val Thr Thr Ser Val Asp Thr Ser Lys Asn Gln Phe
 65                  70                  75                  80

Phe Leu Lys Leu Thr Ser Val Thr Ala Ala Asp Thr Ala Met Tyr Phe
             85                  90                  95

Cys Thr Arg Leu His Gly Arg Tyr Arg Gly Val Gly Arg Leu Ala Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 16
<211> LENGTH: 214
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

Asp Ile Gln Met Thr Gln Ser Pro Ser Thr Leu Ser Ala Ser Val Gly
1               5                   10                  15

Asp Ile Val Thr Ile Thr Cys Arg Ala Ser Gln Ser Ile Gly Asp Trp
            20                  25                  30

Leu Ala Trp Tyr Gln Gln Lys Pro Gly Lys Ala Pro Lys Leu Leu Ile
        35                  40                  45

Tyr Lys Ala Ser Asn Leu Glu Ser Gly Val Pro Ser Arg Phe Ser Gly
50                  55                  60

Ser Gly Ser Gly Thr Glu Phe Thr Leu Thr Ile Ser Ser Leu Gln Ser
65                  70                  75                  80

Asp Asp Phe Ala Thr Tyr Tyr Cys Gln Gln Tyr Asp Ser Tyr Ser Val
                85                  90                  95

Thr Phe Gly Gln Gly Thr Lys Val Glu Ile Lys Gly Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

Gln Val Gln Leu Gln Glu Ala Gly Pro Gly Leu Val Lys Pro Ser Glu
1               5                   10                  15

Thr Leu Ser Leu Thr Cys Thr Val Ser Gly Gly Ser Ile Asn Thr Arg
            20                  25                  30

Asn Tyr Tyr Trp Gly Trp Val Arg Gln Pro Pro Gly Lys Gly Leu Glu
        35                  40                  45

Trp Ile Ala Ser Val Tyr Tyr Thr Gly Ser Thr Phe Tyr Asp Pro Ser
    50                  55                  60

Leu Arg Ser Arg Val Thr Ile Ser Ile Asp Thr Pro Arg Asn Gln Phe
65                  70                  75                  80

Ser Leu Arg Val Ser Ser Val Asp Ala Gly Asp Met Gly Val Tyr Tyr
                85                  90                  95

```
Cys Val Arg Leu Asp Gly Gly Tyr Asn Asn Gly Tyr Tyr Tyr Gly
            100                 105                 110

Met Asp Val Trp Gly Gln Gly Thr Ser Val Thr Val Ser Ser Ala Ser
            115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
            210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
            450                 455

<210> SEQ ID NO 18
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 18

Gly Val Gln Met Thr Gln Ser Pro Ser Thr Leu Ser Ala Ser Val Gly
1               5                   10                  15

Glu Arg Val Thr Val Thr Cys Arg Ala Ser Arg Pro Ile Ser Asn Trp
            20                  25                  30

Leu Ser Trp Tyr Gln Gln Lys Pro Gly Arg Ala Pro Lys Leu Leu Ile
        35                  40                  45

Tyr Gly Thr Ser Thr Leu Glu Ser Gly Val Pro Ser Arg Phe Ser Gly
    50                  55                  60

Ser Gly Ser Gly Thr Glu Phe Thr Leu Thr Ile Thr Asn Leu Gln Pro
65                  70                  75                  80

Asp Asp Phe Ala Thr Tyr Tyr Cys Gln Glu His Asn Leu Tyr Thr Ile
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Gln Leu Gln Leu Gln Glu Ser Gly Pro Gly Leu Val Lys Pro Ser Glu
1               5                   10                  15

Thr Leu Ser Leu Ser Cys Ala Val Ser Gly Ala Ser Ile Arg Ser Asn
            20                  25                  30

Thr Tyr Tyr Trp Gly Trp Ile Arg Gln Pro Pro Gly Arg Gly Leu Glu
        35                  40                  45

Trp Ile Gly Ser Ile Ser His Arg Gly Asp Ala His Tyr Ser Pro Ser
    50                  55                  60

Leu Lys Ser Pro Val Thr Ile Ser Val Asp Thr Ser Lys Asn Glu Phe
65                  70                  75                  80

Ser Leu Lys Ala Thr Ser Val Thr Ala Ala Asp Thr Ala Val Tyr Tyr
                85                  90                  95

Cys Val Ser Leu Ala Tyr Ser Phe Ser Trp Asn Thr Tyr Tyr Phe Tyr
            100                 105                 110

Gly Met Asp Val Trp Gly His Gly Ile Thr Val Thr Val Ser Ser Ala

```
            115                 120                 125
Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 20
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Asp Ile Val Leu Thr Gln Ser Pro Gly Thr Leu Ser Leu Ser Pro Gly
1               5                   10                  15
```

```
Glu Gly Ala Thr Leu Ser Cys Arg Ala Ser Gln Ser Val Asn Ser Gly
            20                  25                  30

Tyr Leu Ala Trp Tyr Gln Lys Pro Gly Gln Pro Pro Arg Leu Leu
        35                  40                  45

Val Phe Ala Ala Ser Ser Arg Ala Thr Gly Ile Ala Asp Arg Phe Arg
 50                  55                  60

Gly Ser Gly Ser Gly Thr Asp Phe Thr Leu Thr Ile Thr Arg Leu Glu
 65                  70                  75                  80

Pro Glu Asp Phe Ala Val Tyr Tyr Cys Gln Leu Tyr Gly His Ser Pro
                 85                  90                  95

Ala Arg Ile Thr Phe Gly Gln Gly Thr Arg Leu Glu Thr Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 21
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Gln Leu Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Ser Ser Ser
            20                  25                  30

Ser Tyr Tyr Trp Gly Trp Ser Arg Gln Ser Pro Gly Lys Gly Leu Glu
        35                  40                  45

Trp Ile Ala Ser Ile Tyr Tyr Ser Gly Ser Thr Tyr Tyr Asn Pro Ser
 50                  55                  60

Leu Lys Ser Arg Val Thr Ile Phe Ile Asp Thr Ser Lys Asn Gln Phe
 65                  70                  75                  80

Ser Leu Lys Leu Ser Ser Val Thr Ala Ala Asp Thr Ala Ile Tyr Tyr
                 85                  90                  95

Cys Ala Arg Val Gly Thr Ser Ala Met Ser Arg Ala Phe Asp Met Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140
```

```
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 22
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Gln Ser
            20                  25                  30

Asn Gly Tyr Asn Tyr Leu Asp Trp Tyr Leu Gln Lys Pro Gly Gln Ser
        35                  40                  45
```

```
Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Lys Val Glu Ala Glu Asp Val Gly Val Tyr Phe Cys Met Gln Ala
                85                  90                  95

Leu Gln Ile Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 23
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

```
Gln Leu Gln Leu Gln Glu Ser Gly Pro Gly Leu Leu Lys Pro Ser Glu
1               5                   10                  15

Thr Leu Ser Leu Thr Cys Thr Val Ser Gly Gly Ser Val Thr Thr Ser
            20                  25                  30

Pro Asp Trp Trp Ala Trp Leu Arg Gln Ser Pro Gly Lys Gly Leu Glu
        35                  40                  45

Trp Ile Gly Ser Val Ser Tyr Thr Gly Arg Thr Val Tyr Asn Pro Ser
    50                  55                  60

Leu Lys Ser Arg Val Thr Ile Ser Leu Asp Thr Ser Lys Asn His Leu
65              70                  75                  80

Ser Leu Arg Met Thr Ser Ala Thr Ala Ala Asp Thr Ala Val Phe Tyr
                85                  90                  95

Cys Ala Arg Leu Thr Pro Ile Asp Arg Phe Ser Ala Asp Tyr Tyr Val
            100                 105                 110

Leu Asp Ile Trp Gly Gln Gly Ala Thr Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175
```

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Lys Thr Tyr Thr
            195                 200                 205

Cys Asn Val Asp His Lys Pro Ser Asn Thr Lys Val Asp Lys Arg Val
        210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
    450

<210> SEQ ID NO 24
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Phe Gln His Lys Pro Gly Gln Ala Pro Arg Leu Leu Ile
        35                  40                  45

Phe Arg Ser Ser Thr Arg Ala Thr Gly Thr Pro Pro Arg Phe Ser Gly
50                  55                  60

Ser Gly Ser Gly Thr Glu Phe Thr Leu Thr Ile Ser Ser Leu Gln Ser

```
            65                  70                  75                  80

Glu Asp Phe Ala Val Tyr Phe Cys Gln His Tyr Ser Tyr Trp Pro Pro
                85                  90                  95

Leu Ile Thr Phe Gly Gln Gly Thr Arg Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 25
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Leu Gln Leu Gln Glu Ser Gly Pro Gly Leu Val Lys Pro Ser Glu
1               5                   10                  15

Thr Leu Ser Leu Ile Cys Thr Val Ser Gly Gly Ser Ile Arg Lys Asn
            20                  25                  30

Asn Glu Trp Trp Ala Trp Ile Arg Gln Ala Pro Gly Lys Gly Leu Glu
        35                  40                  45

Trp Ile Gly Ser Leu Ser Tyr Thr Gly Arg Thr Val Tyr Asn Pro Ser
    50                  55                  60

Leu Lys Ser Arg Val Thr Ile Ser Thr Asp Thr Ser Glu Thr Gln Phe
65                  70                  75                  80

Ser Leu Lys Val Asn Ser Val Thr Ala Ala Asp Thr Ala Val Tyr Tyr
                85                  90                  95

Cys Ala Arg Leu Ser Pro Phe Val Gly Ala Ala Trp Trp Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205
```

```
Asp His Lys Pro Ser Asn Thr Lys Val Asp Lys Arg Val Glu Ser Lys
    210                 215                 220

Tyr Gly Pro Pro Cys Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
                355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
    450

<210> SEQ ID NO 26
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Glu Val Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Ile Gly Thr Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Tyr Ser Pro
                85                  90                  95
```

```
Pro Ala Ile Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 27
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 27

```
Gln Val Arg Leu Gln Glu Ser Gly Pro Gly Leu Val Lys Pro Ser Gly
1               5                   10                  15

Thr Leu Ser Leu Thr Cys Ala Val Ser Gly Gly Ser Ile Tyr Ser Ser
            20                  25                  30

Asn Trp Trp Thr Trp Val Arg Gln Pro Pro Gly Lys Gly Leu Glu Trp
        35                  40                  45

Val Gly Glu Ile His Ile Arg Gly Thr Thr Tyr Tyr Asn Pro Ser Leu
    50                  55                  60

Asn Ser Arg Val Thr Ile Ser Leu Asp Lys Ser Asn Asn Gln Val Ser
65                  70                  75                  80

Leu Arg Leu Thr Ser Val Thr Ala Ala Asp Ser Ala Val Tyr Tyr Cys
                85                  90                  95

Val Ser Gln Glu Val Gly Gly Pro Asp Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
```

```
            225                 230                 235                 240
    Pro Pro Lys Pro Lys Asp Thr Leu Met Ile Ser Arg Thr Pro Glu Val
                    245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
    305                 310                 315                 320

Ser Asn Lys Gly Leu Pro Ser Ser Ile Glu Lys Thr Ile Ser Lys Ala
                    325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
    385                 390                 395                 400

Phe Phe Leu Tyr Ser Arg Leu Thr Val Asp Lys Ser Arg Trp Gln Glu
                    405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440

<210> SEQ ID NO 28
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asn Phe Met Leu Thr Gln Pro His Ser Val Ser Glu Ser Pro Gly Lys
    1               5                   10                  15

Thr Val Thr Ile Ser Cys Thr Arg Ser Gly Gly Ser Ile Ala Thr Tyr
                20                  25                  30

Tyr Val Gln Trp Tyr Gln Gln Arg Pro Gly Ser Ala Pro Thr Asn Val
                35                  40                  45

Ile Tyr Lys Tyr Asp Gln Arg Pro Ser Gly Val Pro Asp Arg Phe Ser
            50                  55                  60

Gly Ser Ile Asp Ser Ser Ser Asn Ser Ala Ser Leu Thr Ile Ser Gly
    65                  70                  75                  80

Leu Lys Thr Glu Asp Glu Ala Asp Tyr Tyr Cys Gln Ser Tyr Asp Asn
                    85                  90                  95

Asn Ile Gln Val Phe Gly Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140
```

```
Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 29
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gln Leu Gln Leu Arg Glu Ser Gly Pro Gly Leu Val Lys Pro Ser Glu
1               5                   10                  15

Thr Leu Ser Leu Thr Cys Ser Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Thr Gly Arg Thr Tyr Tyr Asn Pro Ser
50                  55                  60

Leu Glu Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Gly Leu His Tyr Ser Trp Ser Ala Leu Gly Gly Tyr Tyr Phe
            100                 105                 110

Tyr Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Cys Ser Arg
130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
            210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270
```

```
Asp Val Ser Gln Glu Asp Pro Glu Val Gln Phe Asn Trp Tyr Val Asp
            275                 280                 285

Gly Val Glu Val His Asn Ala Lys Thr Lys Pro Arg Glu Glu Gln Phe
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
            450                 455

<210> SEQ ID NO 30
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Asp Leu Val Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Lys Tyr Gly Ser Ser Pro
                85                  90                  95

Pro Arg Ile Thr Phe Gly Pro Gly Thr Lys Val Asp Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
```

```
                        165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 31
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Arg
            20                  25                  30

Asn Asp Tyr Trp Ala Trp Ile Arg Gln Ser Pro Gly Lys Asp Leu Glu
        35                  40                  45

Trp Ile Gly Thr Ile Ser Phe Ser Gly Ser Thr Phe Tyr Asn Pro Ser
    50                  55                  60

Leu Lys Ser Arg Val Thr Ile Ser Ala Asp Thr Phe Asn Asn His Phe
65                  70                  75                  80

Ser Leu Arg Leu Asp Ala Val Ala Ala Asp Thr Ala Val Tyr Tyr
            85                  90                  95

Cys Ala Arg Leu Ser Pro Phe Val Gly Ala Ala Trp Trp Phe Asp Pro
                100                 105                 110

Trp Gly Pro Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300
```

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly Lys
    450

<210> SEQ ID NO 32
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 32

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Ser Ser Asn
            20                  25                  30

Tyr Leu Gly Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Gly Val Tyr Tyr Cys Gln Arg Tyr Gly Arg Ser Pro
                85                  90                  95

Pro Ala Ile Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

-continued

Lys Val Tyr Ala Cys Glu Val Thr His Gln Gly Leu Ser Ser Pro Val
            195                 200                 205

Thr Lys Ser Phe Asn Arg Gly Glu Cys
    210                 215

<210> SEQ ID NO 33
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Gln Leu Gln Leu Gln Glu Ser Gly Pro Gly Leu Val Lys Pro Ser Glu
1               5                   10                  15

Thr Leu Ser Leu Thr Cys Thr Ala Ser Gly Gly Ser Ile Thr Asn Asn
            20                  25                  30

Ile Asp Tyr Trp Val Trp Ile Arg Gln Pro Pro Gly Arg Gly Leu Glu
        35                  40                  45

Trp Ile Gly Thr Ile Tyr Tyr Ser Gly Ser Thr Phe Tyr Asn Pro Ser
    50                  55                  60

Leu Lys Ser Arg Val Thr Ile Ser Val Asp Thr Ser Asn Asn Gln Phe
65                  70                  75                  80

Ser Leu Asn Leu Asn Ser Met Ser Ala Ala Asp Thr Ala Val Tyr Tyr
                85                  90                  95

Cys Ala Arg Leu Arg Tyr Tyr Asp Ser Asn Gly Tyr Leu Pro Tyr
            100                 105                 110

Trp Ile Asp Ser Trp Gly Gln Gly Thr Leu Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro

```
                325                 330                 335
Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
                420                 425                 430

Ser Val Met His Glu Ala Leu His Asn His Tyr Thr Gln Lys Ser Leu
                435                 440                 445

Ser Leu Ser Leu Gly Lys
            450

<210> SEQ ID NO 34
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Phe Cys Gln Leu Tyr Arg Arg Ser Pro
                85                  90                  95

Pro Arg Leu Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 35
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 35

Gln Leu Gln Leu Gln Glu Ser Gly Pro Gly Leu Val Lys Pro Ser Glu
1               5                   10                  15

Ser Leu Ser Leu Thr Cys Thr Val Ser Gly Ser Ile Ile Ser Asn
            20                  25                  30

Asp Tyr Tyr Trp Ala Trp Ile Arg Gln Ser Pro Gly Lys Gly Leu Glu
            35                  40                  45

Trp Ile Gly Ser Ile Asn Tyr Arg Gly Ser Thr Phe Tyr Ser Pro Ser
50                  55                  60

Leu Asn Ser Arg Val Thr Thr Ser Val Asp Thr Ser Lys Asn Gln Phe
65                  70                  75                  80

Phe Leu Lys Leu Thr Ser Val Thr Ala Ala Asp Thr Ala Met Tyr Phe
                85                  90                  95

Cys Thr Arg Leu His Gly Arg Tyr Arg Gly Val Gly Arg Leu Ala Phe
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
            195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

```
Val Tyr Thr Leu Pro Pro Ser Gln Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450

<210> SEQ ID NO 36
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Asp Ile Gln Met Thr Gln Ser Pro Ser Thr Leu Ser Ala Ser Val Gly
1               5                   10                  15

Asp Ile Val Thr Ile Thr Cys Arg Ala Ser Gln Ser Ile Gly Asp Trp
            20                  25                  30

Leu Ala Trp Tyr Gln Gln Lys Pro Gly Lys Ala Pro Lys Leu Leu Ile
        35                  40                  45

Tyr Lys Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Ser
65                  70                  75                  80

Asp Asp Phe Ala Thr Tyr Tyr Cys Gln Gln Tyr Asp Ser Tyr Ser Val
                85                  90                  95

Thr Phe Gly Gln Gly Thr Lys Val Glu Ile Lys Gly Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 453
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

```
Gln Val Gln Leu Gln Glu Ala Gly Pro Gly Leu Val Lys Pro Ser Glu
1               5                   10                  15

Thr Leu Ser Leu Thr Cys Thr Val Ser Gly Gly Ser Ile Asn Thr Arg
            20                  25                  30

Asn Tyr Tyr Trp Gly Trp Val Arg Gln Pro Pro Gly Lys Gly Leu Glu
        35                  40                  45

Trp Ile Ala Ser Val Tyr Tyr Thr Gly Ser Thr Phe Tyr Asp Pro Ser
    50                  55                  60

Leu Arg Ser Arg Val Thr Ile Ser Ile Asp Thr Pro Arg Asn Gln Phe
65                  70                  75                  80

Ser Leu Arg Val Ser Ser Val Asp Ala Gly Asp Met Gly Val Tyr Tyr
                85                  90                  95

Cys Val Arg Leu Asp Gly Gly Tyr Asn Asn Gly Tyr Tyr Tyr Tyr Gly
            100                 105                 110

Met Asp Val Trp Gly Gln Gly Thr Ser Val Thr Val Ser Ser Ala Ser
        115                 120                 125

Thr Lys Gly Pro Ser Val Phe Pro Leu Ala Pro Cys Ser Arg Ser Thr
130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Gln Phe Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380
```

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
    450

<210> SEQ ID NO 38
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Gly Val Gln Met Thr Gln Ser Pro Ser Thr Leu Ser Ala Ser Val Gly
1               5                   10                  15

Glu Arg Val Thr Val Thr Cys Arg Ala Ser Arg Pro Ile Ser Asn Trp
            20                  25                  30

Leu Ser Trp Tyr Gln Gln Lys Pro Gly Arg Ala Pro Lys Leu Leu Ile
        35                  40                  45

Tyr Gly Thr Ser Thr Leu Glu Ser Gly Val Pro Ser Arg Phe Ser Gly
    50                  55                  60

Ser Gly Ser Gly Thr Glu Phe Thr Leu Thr Ile Thr Asn Leu Gln Pro
65                  70                  75                  80

Asp Asp Phe Ala Thr Tyr Tyr Cys Gln Glu His Asn Leu Tyr Thr Ile
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 39
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gln Leu Gln Leu Gln Glu Ser Gly Pro Gly Leu Val Lys Pro Ser Glu
1               5                   10                  15

Thr Leu Ser Leu Ser Cys Ala Val Ser Gly Ala Ser Ile Arg Ser Asn
            20                  25                  30

Thr Tyr Tyr Trp Gly Trp Ile Arg Gln Pro Pro Gly Arg Gly Leu Glu
        35                  40                  45

Trp Ile Gly Ser Ile Ser His Arg Gly Asp Ala His Tyr Ser Pro Ser
    50                  55                  60

Leu Lys Ser Pro Val Thr Ile Ser Val Asp Thr Ser Lys Asn Glu Phe
65                  70                  75                  80

Ser Leu Lys Ala Thr Ser Val Thr Ala Ala Asp Thr Ala Val Tyr Tyr
                85                  90                  95

Cys Val Ser Leu Ala Tyr Ser Phe Ser Trp Asn Thr Tyr Tyr Phe Tyr
            100                 105                 110

Gly Met Asp Val Trp Gly His Gly Ile Thr Val Thr Val Ser Ser Ala
        115                 120                 125

Ser Thr Lys Gly Pro Ser Val Phe Pro Leu Ala Pro Cys Ser Arg Ser
130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Lys Thr Tyr
        195                 200                 205

Thr Cys Asn Val Asp His Lys Pro Ser Asn Thr Lys Val Asp Lys Arg
210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg

-continued

```
                    405                 410                 415
Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
            435                 440                 445

Ser Leu Ser Leu Gly Lys
        450

<210> SEQ ID NO 40
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Asp Ile Val Leu Thr Gln Ser Pro Gly Thr Leu Ser Leu Ser Pro Gly
1               5                   10                  15

Glu Gly Ala Thr Leu Ser Cys Arg Ala Ser Gln Ser Val Asn Ser Gly
            20                  25                  30

Tyr Leu Ala Trp Tyr Gln Gln Lys Pro Gly Gln Pro Pro Arg Leu Leu
        35                  40                  45

Val Phe Ala Ala Ser Ser Arg Ala Thr Gly Ile Ala Asp Arg Phe Arg
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Leu Tyr Gly His Ser Pro
                85                  90                  95

Ala Arg Ile Thr Phe Gly Gln Gly Thr Arg Leu Glu Thr Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

NICOTINE-BINDING ANTIBODIES

CROSS-REFERENCE TO RELATED APPLICATIONS

This application is the U.S. National Stage of International Application PCT/US2018/046621, which claims priority under 35 U.S.C. § 119(e) to U.S. Provisional Application 62/545,696 filed Aug. 15, 2017, the entire contents of which are incorporated herein by reference.

GOVERNMENT LICENSE RIGHTS

This invention was made with Government support under National Institutes of Health grant RO1 DA038877 awarded by the PHS. The Government has certain rights in the invention.

SEQUENCE LISTING

The instant application contains a Sequence Listing which has been submitted electronically in ASCII format and is hereby incorporated by reference in its entirety.

FIELD

The present disclosure relates generally to the field of antibody therapeutics, specifically antibodies that bind to nicotine. The disclosed nicotine-binding antibodies can be used in methods of aiding smoking cessation and methods of treating nicotine toxicity, including nicotine poisoning and nicotine overdose.

BACKGROUND

The following discussion is merely provided to aid the reader in understanding the disclosure and is not admitted to describe or constitute prior art thereto.

Nicotine is a bitter-tasting, parasympathomimetic alkaloid compound that naturally occurs in large amounts in the leaves of tobacco plants. Nicotine is a nicotinic acetylcholine receptor (nAChR) agonist and functions physiologically as a stimulant. Nicotine is both addictive and toxic, and its ingestion and inhalation have been associated with cardiovascular disease, potential birth defects, and poisoning.

Smoking is a global healthcare problem, largely due to the addictiveness of nicotine. The World Health Organization estimates that there are 1.3 billion smokers worldwide today and nearly five million tobacco-related deaths each year. If current smoking patterns continue, smoking will cause some 10 million deaths each year by 2020. According to the U.S. Center for Disease Control (CDC), tobacco use is the single leading preventable cause of death in the U.S., responsible for approximately 438,000 deaths each year. In addition, it is estimated that smoking results in an annual health-related economic cost of approximately $157 billion. The CDC estimates that, among the 45 million adult smokers in the U.S., 70% want to quit, but less than five percent of those who try to quit remain smoke-free after 12 months.

Addiction to the nicotine in cigarettes and other tobacco products makes it difficult for individuals to quit smoking or using tobacco products. Nicotine is a small molecule that upon inhalation or ingestion into the body quickly passes into the bloodstream and subsequently reaches the brain by crossing the blood-brain barrier. Once in the brain, the nicotine binds to nicotinic receptors, which results in the release of stimulants, such as dopamine, activating the reward system and providing the smoker with a positive and pleasurable re-enforcing experience, which leads to addiction.

Nicotine poisoning, which results from ingestion or inhalation of too much nicotine, is another nicotine-related health problem. The LD50 of nicotine is 50 mg/kg for rats and 3 mg/kg for mice. A dose as low as 30-60 mg (0.5-1.0 mg/kg) may be lethal for adult humans, while children may become ill following ingestion of one cigarette, and ingestion of more than this may cause a child to become severely ill. On the other hand, some evidence suggests that a lethal dose may be as high as 500 mg or more (1.0-7.1 mg/kg) for a human adult. In either case, acute nicotine poisoning usually occurs in children who accidentally chew on nicotine gum or patches or ingest the "e-liquid" of electronic cigarettes. In rare instances, children have also been known to become ill after ingesting cigarettes. There are several hundred cases of acute nicotine poisoning reported every month in the United States alone.

Symptoms of nicotine poisoning can include abdominal cramping, agitation, restlessness, or excitement, a burning sensation in the mouth, headache, vomiting, muscle twitching, fainting, rapid breathing and heartrate, and weakness, as well as more serious complications like convulsions and seizures, coma, and potentially death. The ultimate outlook for a person depends on the amount of nicotine at issue and how quickly treatment is received. The faster a person gets medical help, the better the chance for recovery.

Typically, initial treatment of nicotine poisoning may include the administration of activated charcoal to try to reduce gastrointestinal absorption, while additional treatment may address the symptoms that result from nicotine poisoning.

Thus, there remains a need for effective agents, compositions and methods for aiding smoking cessation and treating nicotine poisoning.

SUMMARY

Described herein are antibodies that bind nicotine, compositions comprising the antibodies, and methods using them for aiding smoking cessation and treating nicotine toxicity, including nicotine poisoning and nicotine overdose.

In one aspect, the present disclosure provides nicotine-binding antibodies or nicotine-binding fragments thereof, comprising the complementarity determining regions (CDRs), the variable regions, or the full heavy chain and light chain of the sequences selected from: the heavy chain sequence of SEQ ID NO: 1 and the light chain sequence of SEQ ID NO: 2; the heavy chain sequence of SEQ ID NO: 3 and the light chain sequence of SEQ ID NO: 4; the heavy chain sequence of SEQ ID NO: 5 and the light chain sequence of SEQ ID NO: 6; the heavy chain sequence of SEQ ID NO: 7 and the light chain sequence of SEQ ID NO: 8; the heavy chain sequence of SEQ ID NO: 9 and the light chain sequence of SEQ ID NO: 10; the heavy chain sequence of SEQ ID NO: 11 and the light chain sequence of SEQ ID NO: 12; the heavy chain sequence of SEQ ID NO: 13 and the light chain sequence of SEQ ID NO: 14; the heavy chain sequence of SEQ ID NO: 15 and the light chain sequence of SEQ ID NO: 16; the heavy chain sequence of SEQ ID NO: 17 and the light chain sequence of SEQ ID NO: 18; the heavy chain sequence of SEQ ID NO: 19 and the light chain sequence of SEQ ID NO: 20; the heavy chain sequence of SEQ ID NO: 21 and the light chain sequence of SEQ ID NO: 22; the heavy chain sequence of SEQ ID NO: 23 and the light chain sequence of SEQ ID NO: 24; the heavy chain sequence of SEQ ID NO: 25 and the light chain sequence of SEQ ID NO: 26; the heavy chain sequence of SEQ ID NO: 27 and the light chain sequence of SEQ ID NO: 28; the heavy chain sequence of SEQ ID NO: 29 and the light chain sequence of SEQ ID NO: 30; the heavy chain sequence of SEQ ID NO: 31 and the light chain sequence of SEQ ID NO: 32; the heavy chain sequence of SEQ ID NO: 33 and the light chain sequence of SEQ ID NO: 34; the heavy chain sequence of SEQ ID NO: 35 and the light chain sequence of SEQ ID NO: 36; the heavy chain sequence of SEQ ID NO: 37 and the light chain sequence of SEQ ID NO: 38; and the heavy chain sequence of SEQ ID NO: 39 and the light chain sequence of SEQ ID NO: 40.

In some embodiments the antibody or fragment may be an IgG4 or derived from an IgG4, and in some embodiments the antibody or fragment may comprise a S228P substitution in its Fc domain.

In some embodiments, the antibody or fragment may be a long-acting variant, such as an antibody or fragment that is conjugated to polyethylene glycol ("PEG"; i.e., the antibody or fragment is PEGylated).

In some embodiments, the antibody or fragment has a $K_D$ for S-(−)-nicotine of less than about 100 nM. For example, in some embodiments, the $K_D$ for S-(−)-nicotine may be less than about 60 nM, less than about 30 nM, less than about 10 nM, or less than about 5 nM.

In some embodiments, the antibody or fragment is substantially not cross-reactive with cotinine or other non-nicotine molecules. For example, in some embodiments, the antibody or fragment is substantially not cross-reactive with one or more nicotine-related compounds selected from cotinine, nicotinamide, B-nicotinamide adenine dinucleotide and nornicotine. In some embodiments, the antibody or fragment is substantially not cross-reactive with one or more smoking-cessation drugs selected from bupropion, varenicline, and cytosine. In some embodiments, the antibody or fragment is substantially not cross-reactive with one more neurotransmitters selected from acetylcholine chloride, 3-hydroxytyramine (dopamine), serotonin, and norepinephrine.

In another aspect, the present disclosure provides pharmaceutical compositions comprising a nicotine-binding antibody or nicotine-binding fragment thereof according to of any one of the embodiments above or disclosed herein and a pharmaceutically acceptable carrier. In some embodiments, the pharmaceutical composition may be formulated for injection or infusion.

In another aspect, the present disclosure provides methods of treating nicotine addiction or facilitating smoking cessation, comprising administering to a mammalian subject in need thereof a therapeutically effective amount of a nicotine-binding antibody or nicotine-binding fragment thereof according to of any one of the embodiments above or disclosed herein, or a pharmaceutical composition comprising the same. In some embodiments, the therapeutically effective amount is effective to reduce plasma levels of nicotine and/or to reduce levels of nicotine localized in the brain. In some embodiments, the subject is a human. In some embodiments, the nicotine addiction is associated with the consumption of a nicotine product selected from tobacco products and electronic cigarettes. In some embodiments, at least one symptom of nicotine withdrawal is reduced, ameliorated, or eliminated.

In some embodiments, the nicotine-binding antibody or nicotine-binding fragment is administered a route of administration selected from the group consisting of intravenously, subcutaneously, intramuscularly, intraperitoneally, orally, nasally, pulmonarily, ocularly, vaginally, or rectally.

In another aspect, the present disclosure provides uses of a nicotine-binding antibody or nicotine-binding fragment thereof according to any one of the embodiments above or disclosed herein in the manufacture of a medicament for the treatment of nicotine addiction or facilitating smoking cessation.

In another aspect, the present disclosure provides nicotine-binding antibodies or nicotine-binding fragments thereof according to any one of the embodiments above or disclosed herein, for use in the treatment of nicotine addiction or facilitating smoking cessation.

In another aspect, the present disclosure provides methods of treating nicotine overdose or nicotine poisoning, comprising administering to a mammalian subject in need thereof a therapeutically effective amount of a nicotine-binding antibody or nicotine-binding fragment thereof according to of any one of the embodiments above or disclosed herein, or a pharmaceutical composition comprising the same. In some embodiments, the therapeutically effective amount is effective to reduce plasma levels of nicotine and/or to reduce levels of nicotine localized in the brain. In some embodiments, the subject is a mammal selected from the group consisting of canines, felines, equines, bovines, and humans. For examples, in some embodiments, the subject is a human child.

In some embodiments, the antibody or nicotine-binding fragment is administered a route of administration selected from the group consisting of intravenously, subcutaneously, intramuscularly, intraperitoneally, orally, nasally, pulmonarily, ocularly, vaginally, or rectally.

In some embodiments, the methods of treating nicotine poisoning or toxicity may further comprise administration of a second compound for treating nicotine overdose or nicotine poisoning, such as activated charcoal.

In another aspect, the present disclosure provides uses of a nicotine-binding antibody or nicotine-binding fragment thereof according to any one of the embodiments above or disclosed herein in the manufacture of a medicament for the treatment of nicotine overdose or nicotine poisoning.

In another aspect, the present disclosure provides nicotine-binding antibodies or nicotine-binding fragments thereof according to any one of the embodiments above or disclosed herein, for use in the treatment of nicotine overdose or nicotine poisoning.

The foregoing general description and following detailed description are exemplary and explanatory and are intended to provide further explanation of the invention.

BRIEF DESCRIPTION OF DRAWINGS

FIG. 1A shows the serum concentration of nicotine in rats that were pre-treated with the disclosed antibodies as a percent of serum levels in control rats that were not treated with antibody. FIG. 1B shows the concentration of nicotine in the brains of rats that were pre-treated with the disclosed antibodies as a percent of the brain levels of control rats that were not treated with antibody.

FIG. 2A shows the serum concentration of nicotine (ng/ml) of rats that were pre-treated with the disclosed antibodies at a dose of 10, 20, or 40 mg/kg. FIG. 2B shows the concentration of nicotine in the brains (ng/g) of rats that were pre-treated with the disclosed antibodies at the same doses.

FIG. 3A shows the serum concentration of nicotine as a percent of serum levels in control rats that were not treated with antibody. FIG. 3B shows the concentration of nicotine in the brain as a percent of brain levels in control rats that were not treated with antibody.

DETAILED DESCRIPTION

Figure 1A:
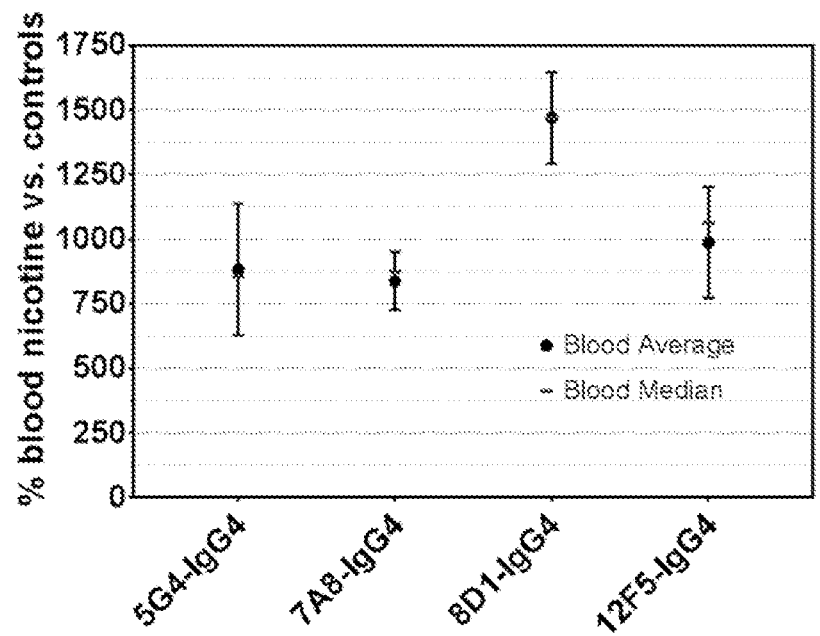
FIGS. 1A and 1B show the results of a nicotine pharmacokinetic study in rats.

Described herein are nicotine-binding antibodies, compositions comprising the antibodies, and methods using them, including for treating nicotine addiction and facilitating nicotine cessation (e.g., smoking cessation) and treating nicotine toxicity, including nicotine poisoning and nicotine overdose.

I. Definitions

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the phrases "therapeutically effective amount" and "therapeutic level" mean that drug dosage or plasma concentration in a subject that provides the specific pharmacological effect for which the drug is administered in a subject in need of such treatment, i.e. to reduce, ameliorate, or eliminate the symptoms or effects of nicotine poisoning or nicotine overdose, and/or treat nicotine addiction and/or facilitate smoking cessation. It is emphasized that a therapeutically effective amount or therapeutic level of a drug will not always be effective in treating the conditions described herein, even though such dosage is deemed to be a therapeutically effective amount by those of skill in the art.

For convenience only, exemplary dosages, drug delivery amounts, therapeutically effective amounts, and therapeutic levels are provided below. Those skilled in the art can adjust such amounts in accordance with standard practices as needed to treat a specific subject and/or condition. The therapeutically effective amount may vary based on the route of administration and dosage form, the age and weight of the subject, and/or the subject's condition, including the amount of nicotine ingested and/or the subject's plasma levels of nicotine at the time of treatment and/or the amount of nicotine localized in the brain at the time of treatment.

The terms "treatment" or "treating" as used herein with reference to nicotine toxicity, nicotine poisoning, and nicotine overdose refer to reducing, ameliorating or eliminating one or more symptoms or effects of nicotine and/or reducing the subject's plasma levels of nicotine and/or reducing the amount of nicotine localized in specific tissues of the subject (e.g., brain/central nervous system, heart and vasculature, etc.).

Alternatively, the terms "treatment" or "treating" as used herein with reference to nicotine addiction or smoking cessation refers to one or more of: reducing, ameliorating or eliminating one or more symptoms or effects of nicotine withdrawal; reducing the daily number of cigarettes or the daily amount of nicotine consumed by a subject; and/or reducing the subject's plasma levels of nicotine and/or reducing the amount of nicotine localized in specific tissues of the subject (e.g., brain/central nervous system, heart and vasculature, etc.).

The terms "individual," "subject," and "patient" are used interchangeably herein, and refer to any individual mammal subject, e.g., bovine, canine, feline, equine, or human.

As used herein, "child" refers to a human subject from 0 through about 18 years of age. A child can be a subject that begins a course of treatment prior to turning about 18 years of age, even if the subject continues treatment beyond 18 years of age.

II. Nicotine, Addiction, and Toxicity

Nicotine is a nitrogen-containing chemical made by several types of plants including tobacco and other members of the nightshade family. When humans, mammals and most other types of animals are exposed to nicotine, it increases their heart rate, heart muscle oxygen consumption rate, and heart stroke volume. The consumption of nicotine is also linked to raised alertness, euphoria, and a sensation of being relaxed. However, nicotine is highly addictive.

By binding to nicotinic acetylcholine receptors in the brain, nicotine elicits its psychoactive effects and increases the levels of several neurotransmitters in various brain structures. Nicotine has a higher affinity for nicotinic receptors in the brain than those in skeletal muscle, though at toxic doses it can induce contractions and respiratory paralysis. Nicotine's selectivity is thought to be due to a particular amino acid difference on these receptor subtypes. The structure of nicotine is shown in Formula I below.

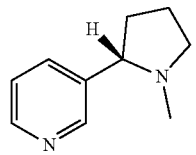

Formula I

People who regularly consume nicotine and then suddenly stop experience withdrawal symptoms, which may include cravings, a sense of emptiness, anxiety, depression, moodiness, irritability, and inattentiveness. The American Heart Association says that nicotine (from smoking tobacco) is one of the hardest substances to quit, at least as hard as heroin.

The methods described herein useful in treating nicotine addiction and/or facilitating smoking cessation (or the cessation of use of other tobacco or nicotine products) in a mammalian subject in need thereof, use nicotine-binding antibodies, which bind nicotine and prevent it from interacting with nicotinic acetylcholine receptors.

Nicotine poisoning or nicotine overdose can occur when an individual consumes loose tobacco, cigarettes, nicotine gum, patches, or the "e-liquid" of electronic cigarettes (e.g., the nicotine-containing liquid that is used in electronic cigarettes and other vaporizing devices). Indeed, a recent study showed that the incidence of nicotine poisoning from exposure to e-cigarettes increased 1492.9% between January 2012 and April 2015 (Kamboj et al. PEDIATRICS 137(6): e20160041 (2016)). Although exposure can occur through inhalation of tobacco smoke (either primary or second hand), nicotine poisoning or nicotine overdose more commonly results when a subject (typically a child) ingests nicotine, for example by chewing or ingesting nicotine gum, ingesting cigarettes or other tobacco leaf products, ingesting nicotine patches, or ingesting e-liquid. Additionally, nicotine can be dermally absorbed, and therefore nicotine poisoning can result from toxic levels of nicotine coming into direct contact with the skin.

Nicotine poisoning can produce neurological symptoms (convulsions, coma, depression, confusion, fainting, headache), cardiovascular symptoms (rapid heartbeat, high blood pressure), respiratory symptoms (difficulty breathing, rapid breathing), gastrointestinal symptoms (increased salivation, abdominal cramps, vomiting), and musculoskeletal symptoms (Muscular twitching, weakness), as well as death.

The methods described herein for treating nicotine toxicity, including nicotine poisoning and nicotine overdose, use an antibody that binds nicotine, thereby sequestering it and preventing the nicotine from binding a cognate receptor or crossing the blood-brain barrier. In some embodiments, a pharmaceutical composition comprising such an antibody is administered in a therapeutically effective amount, such as an amount effective to reduce plasma levels of nicotine and/or to reduce levels of nicotine localized in the brain.

III. Nicotine-Binding Antibodies

In some embodiments, the disclosed methods comprise administering to a mammalian subject in need thereof a therapeutically effective amount of a nicotine-binding antibody, a nicotine-binding fragment thereof, a related construct capable of binding nicotine, or a pharmaceutical composition comprising the same. For convenience, these agents are referred to collectively herein as "nicotine-binding antibodies."

Anti-nicotine antibodies have been previously developed, primarily for the purpose of facilitating smoking cessation. See, e.g., WO 2002/058635; WO 2000/032239; WO 2003/082329; U.S. Patent Application Publication 2006/111271; U.S. Pat. Nos. 8,344,111; 8,232,072; 6,232,082; 7,547,712; 7,446,205; and Carrera et al., "Investigations using immunization to attenuate the psychoactive effects of nicotine," *Bioorg Med Chem* 12(3):563-70 (2004). These patents, applications, and non-patent literature are incorporated by reference herein to the extent that they relate to anti-nicotine antibodies and related constructs including nicotine-binding antibody fragments. However, the antibodies disclosed herein are novel, and may be used not only for facilitating smoking cessation, but also for treating nicotine toxicity.

Nicotine is a small, haptenic molecule and typically is coupled to an immunogenic carrier, such as an immunogenic protein, to elicit an immune response and induce the production of nicotine-binding antibodies. General techniques for making antibodies can be employed. See, e.g., Kohler and Milstein, *Eur. J. Immunol.*, 5: 511-519 (1976); Harlow and Lane (eds.), ANTIBODIES: A LABORATORY MANUAL, CSH Press (1988); C. A. Janeway et al. (eds.), IMMUNOBIOLOGY, 5th Ed., Garland Publishing, New York, N.Y. (2001).

Anti-nicotine antibodies useful in the methods described herein can be obtained by any means, including via in vitro sources (e.g., a hybridoma or a cell line producing an antibody recombinantly) and in vivo sources (e.g., rodents, rabbits, humans, etc.). Human, partially humanized, fully humanized, and chimeric antibodies can be made by methods known in the art, such as using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the HUMAB-MOUSE™, the Kirin TC MOUSE™, and the KM-MOUSE™ (see, e.g., Lonberg, *Nat. Biotechnol.*, 23(9): 1117-25 (2005), and Lonberg, Handb. Exp. Pharmacol., 181: 69-97 (2008)).

Nicotine-binding antibodies used in the methods disclosed herein generally will be monoclonal and/or recombinant. Monoclonal antibodies (mAbs) may obtained by methods known in the art, for example, by fusing antibody-producing cells with immortalized cells to obtain a hybridoma, and/or by generating mAbs from mRNA extracted from bone marrow, B cells, and/or spleen cells of immunized animals using combinatorial antibody library technology and/or by isolating monoclonal antibodies from serum from subjects immunized with a nicotine antigen. Recombinant antibodies may be obtained by methods known in the art, for example, using phage display technologies, yeast surface display technologies (Chao et al., Nat. Protoc., 1(2): 755-68 (2006)), mammalian cell surface display technologies (Beerli et al., PNAS, 105(38): 14336-41 (2008), and/or expressing or co-expressing antibody polypeptides. Other techniques for making antibodies are known in the art, and can be used to obtain antibodies used in the methods described herein.

Typically, an antibody consists of four polypeptides: two identical copies of a heavy (H) chain polypeptide and two copies of a light (L) chain polypeptide. Typically, each heavy chain contains one N-terminal variable ($V_H$) region and three C-terminal constant ($C_H1$, $C_H2$ and $C_H3$) regions, and each light chain contains one N-terminal variable ($V_L$) region and one C-terminal constant ($C_L$) region. The variable regions of each pair of light and heavy chains form the antigen binding site of an antibody.

The terms "antibody fragment" and "nicotine-binding fragment," as used herein, refer to one or more portions of a nicotine-binding antibody that exhibits the ability to bind nicotine. Examples of binding fragments include (i) Fab fragments (monovalent fragments consisting of the $V_L$, $V_H$, $C_L$ and $C_{H1}$ domains); (ii) F(ab')2 fragments (bivalent fragment comprising two Fab fragments linked by a disulfide bridge at the hinge region); (iii) Fd fragments (comprising the $V_H$ and $C_{H1}$ domains); (iv) Fv fragments (comprising the $V_L$ and $V_H$ domains of a single arm of an antibody), (v) dAb fragments (comprising a $V_H$ domain); and (vi) isolated complementarity determining regions (CDR), e.g., $V_H$ CDR3. Other examples include single chain Fv (scFv) constructs. See e.g., Bird et al., Science, 242:423-26 (1988); Huston et al., *Proc. Natl. Acad. Sci. USA*, 85:5879-83 (1988). Other examples include nicotine-binding domain immunoglobulin fusion proteins comprising (i) a nicotine-binding domain polypeptide (such as a heavy chain variable region, a light chain variable region, or a heavy chain variable region fused to a light chain variable region via a linker peptide) fused to an immunoglobulin hinge region polypeptide, (ii) an immunoglobulin heavy chain $C_{H2}$ constant region fused to the hinge region, and (iii) an immunoglobulin heavy chain $C_{H3}$ constant region fused to the $C_{H2}$ constant region, where the hinge region may be modified by replacing one or more cysteine residues with, for example, serine residues, to prevent dimerization. See, e.g., U.S. Patent Application 2003/0118592; U.S. Patent Application U.S. 2003/0133939.

In some embodiments, a nicotine-binding antibody as disclosed herein is a human IgG1 antibody or a human IgG4 antibody. In some embodiments, the nicotine-binding antibody is mammalian, human, humanized, or chimeric.

In some embodiments, nicotine-binding antibodies as disclosed herein comprise one or more mutations that make the antibody more suitable in a therapeutic context.

Heavy and light chain sequences of exemplary novel IgG1 nicotine-binding antibodies are disclosed in Table 1 below. Heavy and light chain sequences of exemplary novel IgG4 nicotine-binding antibodies are disclosed in Table 2 below.

TABLE 1

Heavy and Light Chain Sequences of IgG1 Nicotine-Binding Antibodies

| Antibody Chain | Amino Acid Sequence | SEQ ID NO: |
|---|---|---|
| 8D1 Heavy | QVRLQESGPGLVKPSGTLSLTCAVSGGSIYSSNWWTWVRQPPGKGLE WVGEIHIRGTTYYNPSLNSRVTISLDKSNNQVSLRLTSVTAADSAVY YCVSQEVGGPDLWGQGTLVTVSS*ASTKGPSVFPLAPSSKSTSGGTAA LGCLVKDYFPEPVTVSWNSGALTSGVHTFPAVLQSSGLYSLSSVVTV PSSSLGTQTYICNVNHKPSNTKVDKKVEPKSCDKTHTCPPCPAPELL GGPSVFLFPPKPKDTLMISRTPEVTCVVVDVSHEDPEVKFNWYVDGV EVHNAKTKPREEQYNSTYRVVSVLTVLHQDWLNGKEYKCKVSNKALP APIEKTISKAKGQPREPQVYTLPPSRDELTKNQVSLTCLVKGFYPSD IAVEWESNGQPENNYKTTPPVLDSDGSFFLYSKLTVDKSRWQQGNFF SCSVMHEALHNHYTQKSLSLSPGK* | 1 |
| 8D1 Light | NFMLTQPHSVSESPGKTVTISCTRSGGSIATYYVQWYQQRPGSAPTN VIYKYDQRPSGVPDRFSGSIDSSSNSASLTISGLKTEDEADYYCQSY DNNIQVFGGGTKLTVL*GQPKAAPSVTLFPPSSEELQANKATLVCLIS DFYPGAVTVAWKADGSPVKAGVETTKPSKQSNNKYAASSYLSLTPEQ WKSHRSYSCQVTHEGSTVEKTVAPTECS* | 2 |
| 12F5 Heavy | QLQLQESGPGLVKPSETLSLICTVSGGSIRKNNEWWAWIRQAPGKGL EWIGSLSYTGRTVYNPSLKSRVTISTDTSETQFSLKVNSVTAADTAV YYCARLSPFVGAAWWFDPWGQGTLVTVSS*ASTKGPSVFPLAPSSKST SGGTAALGCLVKDYFPEPVTVSWNSGALTSGVHTFPAVLQSSGLYSL SSVVTVPSSSLGTQTYICNVNHKPSNTKVDKKVEPKSCDKTHTCPPC PAPELLGGPSVFLFPPKPKDTLMISRTPEVTCVVVDVSHEDPEVKFN WYVDGVEVHNAKTKPREEQYNSTYRVVSVLTVLHQDWLNGKEYKCKV SNKALPAPIEKTISKAKGQPREPQVYTLPPSRDELTKNQVSLTCLVK GFYPSDIAVEWESNGQPENNYKTTPPVLDSDGSFFLYSKLTVDKSR WQQGNFFSCSVMHEALHNHYTQKSLSLSPGK* | 3 |
| 12F5 Light | EVVLTQSPGTLSLSPGERATLSCRASQSVSSRYLAWYQQKPGQAPRL LIYGASSRAIGTPDRFSGSGSGTDFTLTISRLEPEDFAVYYCQQYAY SPPAITFGGGTKVEIK*RTVAAPSVFIFPPSDEQLKSGTASVFCLLNN FYPREAKVQWKVDNALQSGNSQESVTEQDSKDSTYSLSSTLTLSKAD YEKHKVYACEVTHQGLSSPVTKSFNRGEC* | 4 |
| 7A8 Heavy | QLQLQESGPGLLKPSETLSLTCTVSGGSVTTSPDWWAWLRQSPGKGL EWIGSVSYTGRTVYNPSLKSRVTISLDTSKNHLSLRMTSATAADTAV FYCARLTPIDRFSADYYVLDIWGQGATVTVSS*ASTKGPSVFPLAPSS KSTSGGTAALGCLVKDYFPEPVTVSWNSGALTSGVHTFPAVLQSSGL YSLSSVFTVPSSSLGTQTYICNVNHKPSNTKVDKKVEPKSCDKTHTC PPCPAPELLGGPSVFLFPPKPKDTLMISRTPEVTCVVVDVSHEDPEV KFNWYVDGVEVHNAKTKPREEQYNSTYRVVSVLTVLHQDWLNGKEYK CKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSMHEALHNHYTQKSLSLSPGK* | 5 |
| 7A8 Light | EIVMTQSPATLSVSPGERATLSCRASQSISSNLAWFQHKPGQAPRLL IFRSSTRATGTPPRFSGSGSGTEFTLTISSLQSEDFAVYFCQHYSYW PPLITFGQGTRLEIK*RTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC* | 6 |

TABLE 1-continued

Heavy and Light Chain Sequences of IgG1 Nicotine-Binding Antibodies

| Antibody Chain | Amino Acid Sequence | SEQ ID NO: |
|---|---|---|
| 5DI Heavy | QLQLRESGPGLVKPSETLSLTCSVSGGSISSSSYYWGWIRQPPGKGL EWIGSIYYTGRTYYNPSLESRVTISVDTSKNQFSLKLSSVTAADTAI YYCAGLHYSWSALGGYYFYGMDVWGQGTTVTVSS*ASTKGPSVFPLAP SSKSTSGGTAALGCLVKDYFPEPVTVSWNSGALTSGVHTFPAVLQSS GLYSLSSVVTVPSSSLGTQTYICNVNHKPSNTKVDKKVEPKSCDKTH TCPPCPAPELLGGPSVFLFPPKPKDTIMISRTPEVTCVVVDVSHEDP EVKFNWYVDGVEVHNAKTKPREEQYNSTYRVVSVLTVLHQDWLNGKE YKCKVSNKALPAPIEKTISKAKGQPREPQVYTLPPSRDELTKNQVSL TCLVKGFYPSDIAVEWESNGQPENNYKTTPPVLDSDGSFFLYSKLTV DKSRWQQGNVFSCSMHEALHNHYTQKSLSLSPGK* | 7 |
| 5DI Light | EIVLTQSPGTLSLSPGERATLSCRASQSVSSRDLVWYQQKPGQAPRL LIYGASTRATGIPDRFSGSGSGTDFTLTISRLEPEDFAVYYCQKYGS SPPRITFGPGTKVDIK*RTVAAPSVFIFPPSDEQLKSGTASVVCLLNN FYPREAKVQWKVDNALQSGNSQESVTEQDSKDSTYSLSSTLTLSKAD YEKHKVYACEVTHQGLSSPVTKSFNRGEC* | 8 |
| 5G4 Heavy | QLQLQESGPGLVKPSETLSLTCSVSGGSISSSSYYWGWSRQSPGKGL EWIASIYYSGSTYYNPSLKSRVTIFIDTSKNQFSLKLSSVTAADTAI YYCARVGTSAMSRAFDMWGQGTMVTVSS*ASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKKVEPKSCDKTHTCPPCP APELLGGPSVFLFPPKPKDTLMISRTPEVTCVVVDVSHEDPEVKFNW YVDGVEVHNAKTKPREEQYNSTYRVVSVLTVLHQDWLNGKEYKCKVS NKALPAPIEKTISKAKGQPREPQVYTLPPSRDELTKNQVSLTCLVKG FYPSDIAVEWESNGQPENNYKTTPPVLDSDGSFFLYSKLTVDKSRWQ QGNFFSCSMHEALHNHYTQKSLSLSPGK* | 9 |
| 5G4 Light | DIVMTQSPLSLPVTPGEPASISCRSSQSLLQSNGYNYLDWYLQKPGQ SPQLLIYLGSNRASGVPDRFSGSGSGTDFTLKISKVEAEDVGVYFCM QALQIPWTFGQGTKVEIK*RTVAAPSVFIFPPSDEQLKSGTASVFCLL NNFYPREAKVQWKVDNALQSGNSQESVTEQDSKDSTYSLSSTLTLSK ADYEKHKVYACEVTHQGLSSPVTKSFNRGEC* | 10 |
| 5H1 Heavy | QVQLQESGPGLVKPSETLSLTCTVSGGSISRRNDYWAWIRQSPGKDL EWIGTISFSGSTFYNPSLKSRVTISADTFNNHFSLRLDAVAAADTAI YYCARLSPFVGAAWWFDPWGPGTLVTVSS*ASTKGPSVFPLAPSSKST SGGTAALGCLVKDYFPEPVTVSWNSGALTSGVHTFPAVLQSSGLYSL SSVVTVPSSSLGTQTYICNVNHKPSNTKVDKKVEPKSCDKTHTCPPC PAPELLGGPSVFLFPPKPKDTLMISRTPEVTCVVVDVSHEDPEVKFN WYVDGVEVHNAKTKPREEQYNSTYRVVSVLTVLHQDWLNGKEYKCKV SNKALPAPIEKTISKAKGQPREPQVYTLPPSRDELTKNQVSLTCLVK GFYPSDIAVEWESNGQPENNYKTTPPVLDSDGSFFLYSKLTVDKSRW QQGNVFSCSVMHEALHNHYTQKSLSLSPGK* | 11 |
| 5H1 Light | EIVLTQSPGTLSLSPGERATLSCRASQSLSSNYLGWYQQKPGQAPRL LIYGASNRATGIPDRFSGSGSGTDFTLTISRLEPEDFGVYYCQRYGR SPPAITFGGGTKVEIK*RTVAAPSVFIFPPSDEQLKSGTASVVCLLNN FYPREAKVQWKVDNALQSGNSQESVTEQDSKDSTYSLSSTLTLSKAD YEKHKVYACEVTHQGLSSPVTKSFNRGEC* | 12 |
| 15A4 Heavy | QLQLQESGPGLVKPSETLSLTCTASGGSITNNIDYWVWIRQPPGRGL EWIGTIYYSGSTFYNPSLKSRVTISVDTSNNQFSLNLNSMSAADTAV YYCARLRYYYDSNGYLPYWIDSWGQGTLVTVSS*ASTKGPSVFPLAPS SKSTSGGTAALGCLVKDYFPEPVTVSWNSGALTSGVHTFPAVLQSSG LYSLSSVVTVPSSSLGTQTYICNVNHKPSNTKVDKKVEPKSCDKTHT CPPCPAPELLGGPSVFLFPPKPKDTLMISRTPEVTCVVVDVSHEDPE VKFNWYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESNGQPENNYKTTPPVLDSDGSFFLYSKLTVD KSRWQQGNVFSCSMHEALHNHYTQKSLSLSPGK* | 13 |
| 15A4 Light | EIVLTQSPGTLSLSPGERATLSCRASQSISSSYLGWYQQKPGQAPRL LIYGASSRATGIPDRFSGSGSGTDFTLTISSLEPEDFAVYFCQLYRR SPPRLTFGGGTKVEIK*RTVAAPSVFIFPPSDEQLKSGTASVVCLLNN FYPREAKVQWKVDNALQSGNSQESVTEQDSKDSTYSLSSTLTLSKAD YEKHKVYACEVTHQGLSSPVTKSFNRGEC* | 14 |
| 2E11 Heavy | QLQLQESGPGLVKPSESLSLTCTVSGGSIISNDYYWAWIRQSPGKGL EWIGSINYRGSTFYSPSLNSRVTTSVDTSKNQFFLKLTSVTAADTAM YFCTRLHGRYRGVGRLAFDYWGQGTLVTVSS*ASTKGPSVFPLAPSSK STSGGTAALGCLVKDYFPEPVTVSWNSGALTSGVHTFPAVLQSSGLY SLSSVFTVPSSSLGTQTYICNVNHKPSNTKVDKKVEPKSCDKTHTCP PCPAPELLGGPSVFLFPPKPKDTLMISRTPEVTCVVVDVSHEDPEVK* | 15 |

TABLE 1-continued

Heavy and Light Chain Sequences of IgG1
Nicotine-Binding Antibodies

| Antibody Chain | Amino Acid Sequence | SEQ ID NO: |
|---|---|---|
| | *FNWYVDGVEVHNAKTKPREEQYNSTYRVVSVLTVLHQDWLNGKEYKC KVSNKALPAPIEKTISKAKGQPREPQVYTLPPSRDELTKNQVSLTCL VKGFYPSDIAVEWESNGQPENNYKTTPPVLDSDGSFFLYSKLTVDKS RWQQGNVFSCSMHEALHNHYTQKSLSLSPGK* | |
| 2E11 Light | DIQMTQSPSTLSASVGDIVTITCRASQSIGDWLAWYQQKPGKAPKLL IYKASNLESGVPSRFSGSGSGTEFTLTISSLQSDDFATYYCQQYDSY SVTFGQGTKVEIK*GTVAAPSVHFPPSDEQLKSGTASVFCLLNNFYPR EAKVQWKVDNALQSGNSQESVTEQDSKDSTYSLSSTLTLSKADYEKH KVYACEVTHQGLSSPVTKSFNRGEC* | 16 |
| 13F7 Heavy | QVQLQEAGPGLVKPSETLSLTCTVSGGSINTRNYYWGWVRQPPGKGL EWIASVYYTGSTFYDPSLRSRVTISIDTPRNQFSLRVSSVDAGDMGV YYCVRLDGGYNNGYYYYGMDVWGQGTSVTVSS*ASTKGPSVFPLAPSS KSTSGGTAALGCLVKDYFPEPVTVSWNSGALTSGVHTFPAVLQSSGL YSLSSVVTVPSSSLGTQTYICNVNHKPSNTKVDKKVEPKSCDKTHTC PPCPAPELLGGPSVFLFPPKPKDTIMISRTPEVTCVVVDVSHEDPEV KFNWYVDGVEVHNAKTKPREEQYNSTYRVVSVLTVLHQDWLNGKEYK CKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSMHEALHNHYTQKSLSLSPGK* | 17 |
| 13F7 Light | GVQMTQSPSTLSASVGERVTVTCRASRPISNWLSWYQQKPGRAPKLL IYGTSTLESGVPSRFSGSGSGTEFTLTITNLQPDDFATYYCQEHNLY TITFGPGTKVEIK*RTVAAPSVHFPPSDEQLKSGTASVFCLLNNFYPR EAKVQWKVDNALQSGNSQESVTEQDSKDSTYSLSSTLTLSKADYEKH KVYACEVTHQGLSSPVTKSFNRGEC* | 18 |
| 8H5 Heavy | QLQLQESGPGLVKPSETLSLSCAVSGASIRSNTYYWGWIRQPPGRGL EWIGSISHRGDAHYSPSLKSPVTISVDTSKNEFSLKATSVTAADTAV YYCVSLAYSFSWNTYYFYGMDVWGHGITVTVSS*ASTKGPSVFPLAPS SKSTSGGTAALGCLVKDYFPEPVTVSWNSGALTSGVHTFPAVLQSSG LYSLSSVVTVPSSSLGTQTYICNVNHKPSNTKVDKKVEPKSCDKTHT CPPCPAPELLGGPSVFLFPPKPKDTLIVISRTPEVTCVVVDVSHEDP EVKFNWYVDGVEVHNAKTKPREEQYNSTYRVVSVLTVLHQDWLNGKE YKCKVSNKALPAPIEKTISKAKGQPREPQVYTLPPSRDELTKNQVSL TCLVKGFYPSDIAVEWESNGQPENNYKTTPPVLDSDGSFFLYSKLTV DKSRWQQGNVFSCSMHEALHNHYTQKSLSLSPGK* | 19 |
| 8H5 Light | DIVLTQSPGTLSLSPGEGATLSCRASQSVNSGYLAWYQQKPGQPPRL LVFAASSRATGIADRFRGSGSGTDFTLTITRLEPEDFAVYYCQLYGH SPARITFGQGTRLETK*RTVAAPSVFIFPPSDEQLKSGTASVVCLLNN FYPREAKVQWKVDNALQSGNSQESVTEQDSKDSTYSLSSTLTLSKAD YEKHKVYACEVTHQGLSSPVTKSFNRGEC* | 20 |

Heavy and light chain complementarity determining regions (CDRs) are shown in bold, underlined text.
CDR annotation was made according to IMGT numbering.
Constant regions are denoted in italicized, underlined text.

TABLE 2

Heavy and Light Chain Sequences of IgG4
Nicotine-Binding Antibodies

| Antibody Chain | Amino Acid Sequence | SEQ ID NO: |
|---|---|---|
| 5G4-IgG4 Heavy | QLQLQESGPGLVKPSETLSLTCSVSGGSISSSSYYWGWSRQSPGKGL EWIASIYYSGSTYYNPSLKSRVTIFIDTSKNQFSLKLSSVTAADTAI YYCARVGTSAMSRAFDMWGQGTMVTVSS*ASTKGPSVFPLAPCSRSTS ESTAALGCLVKDYFPEPVTVSWNSGALTSGVHTFPAVLQSSGLYSLS SVVTVPSSSLGTKTYTCNVDHKPSNTKVDKRVESKYGPPCPPCPAPE FLGGPSVFLFPPKPKDTLMISRTPEVTCVVVDVSQEDPEVQFNWYVD GVEVHNAKTKPREEQFNSTYRVVSVLTVLHQDWLNGKEYKCKVSNKG LPSSIEKTISKAKGQPREPQVYTLPPSQEEMTKNQVSLTCLVKGFYP SDIAVEWESNGQPENNYKTTPPVLDSDGSFFLYSRLTVDKSRWQEGN VFSCSVMHEALHNHYTQKSLSLSLGK* | 21 |

TABLE 2-continued

Heavy and Light Chain Sequences of IgG4 Nicotine-Binding Antibodies

| Antibody Chain | Amino Acid Sequence | SEQ ID NO: |
|---|---|---|
| 5G4-IgG4 Light | DIVMTQSPLSLPVTPGEPASISCRSSQSLLQSNGYNYLDWYLQKPGQ SPQLLIYLGSNRASGVPDRFSGSGSGTDFTLKISKVEAEDVGVYFCM QALQIPWTFGQGTKVEIK*RTVAAPSVFIFPPSDEQLKSGTASVVCLL NNFYPREAKVQWKVDNALQSGNSQESVTEQDSKDSTYSLSSTLTLSK ADYEKHKVYACEVTHQGLSSPVTKSFNRGEC* | 22 |
| 7A8-IgG4 Heavy | QLQLQESGPGLLKPSETLSLTCTVSGGSVTTSPDWWAWLRQSPGKGL EWIGSVSYTGRTVYNPSLKSRVTISLDTSKNHLSLRMTSATAADTAV FYCARLTPIDRFSADYYVLDIWGQGATVTVSS*ASTKGPSVFPLAPCS RSTSESTAALGCLVKDYFPEPVTVSWNSGALTSGVHTFPAVLQSSGL YSLSSVFTVPSSSLGTKTYTCNVDHKPSNTKVDKRVESKYGPPCPPC PAPEFLGGPSVFLFPPKPKDTLMISRTPEVTCVVVDVSQEDPEVQFN WYVDGVEVHNAKTKPREEQFNSTYRVVSVLTVLHQDWLNGKEYKCKV SNKGLPSSIEKTISKAKGQPREPQVYTLPPSQEEMTKNQVSLTCLVK GFYPSDIAVEWESNGQPENNYKTTPPVLDSDGSFFLYSRLTVDKSRW QEGNFFSCSVMHEALHNHYTQKSLSLSLGK* | 23 |
| 7A8-IgG4 Light | EIVMTQSPATLSVSPGERATLSCRASQSISSNLAWFQHKPGQAPRLL IFRSSTRATGTPPRFSGSGSGTEFTLTISSLQSEDFAVYFCQHYSYW PPLITFGQGTRLEIK*RTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC* | 24 |
| 12F5-IgG4 Heavy | QLQLQESGPGLVKPSETLSLICTVSGGSIRKNNEWWAWIRQAPGKGL EWIGSLSYTGRTVYNPSLKSRVTISTDTSETQFSLKVNSVTAADTAV YYCARLSPFVGAAWWFDPWGQGTLVTVSS*ASTKGPSVFPLAPCSRST SESTAALGCLVKDYFPEPVTVSWNSGALTSGVHTFPAVLQSSGLYSL SSVVTVPSSSLGTKTYTCNVDHKPSNTKVDKRVESKYGPPCPPCPAP EFLGGPSVFLFPPKPKDTLMISRTPEVTCVVVDVSQEDPEVQFNWYV DGVEVHNAKTKPREEQFNSTYRVVSVLTVLHQDWLNGKEYKCKVSNK GLPSSIEKTISKAKGQPREPQVYTLPPSQEEMTKNQVSLTCLVKGFY PSDIAVEWESNGQPENNYKTTPPVLDSDGSFFLYSRLTVDKSRWQEG NFFSCSVMHEALHNHYTQKSLSLSLGK* | 25 |
| 12F5-IgG4 Light | EVVLTQSPGTLSLSPGERATLSCRASQSVSSRYLAWYQQKPGQAPRL LIYGASSRAIGTPDRFSGSGSGTDFTLTISRLEPEDFAVYCQQYAY SPPAITFGGGTKVEIK*RTVAAPSVFIFPPSDEQLKSGTASVFCLLNN FYPREAKVQWKVDNALQSGNSQESVTEQDSKDSTYSLSSTLTLSKAD YEKHKVYACEVTHQGLSSPVTKSFNRGEC* | 26 |
| 8D1-IgG4 Heavy | QVRLQESGPGLVKPSGTLSLTCAVSGGSIYSSNWWTWVRQPPGKGLE WVGEIHIRGTTYYNPSLNSRVTISLDKSNNQVSLRLTSVTAADSAVY YCVSQEVGGPDLWGQGTLVTVSS*ASTKGPSVFPLAPCSRSTSESTAA LGCLVKDYFPEPVTVSWNSGALTSGVHTFPAVLQSSGLYSLSSVVTV PSSSLGTKTYTCNVDHKPSNTKVDKRVESKYGPPCPPCPAPEFLGGP SVFLFPPKPKDTLMISRTPEVTCVVVDVSQEDPEVQFNWYVDGVEVH NAKTKPREEQFNSTYRVVSVLTVLHQDWLNGKEYKCKVSNKGLPSSI EKTISKAKGQPREPQVYTLPPSQEEMTKNQVSLTCLVKGFYPSDIAV EWESNGQPENNYKTTPPVLDSDGSFFLYSRLTVDKSRWQEGNFFSCS MHEALHNHYTQKSLSLSLGK* | 27 |
| 8D1-IgG4 Light | NFMLTQPHSVSESPGKTVTISCTRSGGSIATYYVQWYQQRPGSAPTN VIYKYDQRPSGVPDRFSGSIDSSSNSASLTISGLKTEDEADYYCQSY DNNIQVFGGGTKLTVL*GQPKAAPSVTLFPPSSEELQANKATLVCLIS DFYPGAVTVAWKADGSPVKAGVETTKPSKQSNNKYAASSYLSLTPEQ WKSHRSYSCQVTHEGSTVEKTVAPTECS* | 28 |
| 5D1-IgG4 Heavy | QLQLRESGPGLVKPSETLSLTCSVSGGSISSSSYYWGWIRQPPGKGL EWIGSIYYTGRTYYNPSLESRVTISVDTSKNQFSLKLSSVTAADTAV YYCAGLHYSWSALGGYYFYGMDVWGQGTTVTVSS*ASTKGPSVFPLAP CSRSTSESTAALGCLVKDYFPEPVTVSWNSGALTSGVHTFPAVLQSS GLYSLSSVVTVPSSSLGTKITTCNVDHKPSNTKVDKRVESKYGPPCP PCPAPEFLGGPSVFLFPPKPKDTLMISRTPEVTCVVVDVSQEDPEVQ FNWYVDGVEVHNAKTKPREEQFNSTYRVVSVLTVLHQDWLNGKEYKC KVSNKGLPSSIEKTISKAKGQPREPQVYTLPPSQEEMTKNQVSLTCL VKGFYPSDIAVEWESNGQPENNYKTTPPVLDSDGSFFLYSRLTVDKS RWQEGNVFSCSMHEALHNHYTQKSLSLSLGK* | 29 |
| 5D1-IgG4 Light | EIVLTQSPGTLSLSPGERATLSCRASQSVSSRDLVWYQQKPGQAPRL LIYGASTRATGIPDRFSGSGSGTDFTLTISRLEPEDFAVYYCQKYGS SPPRITFGPGTKVDIK*RTVAAPSVFIFPPSDEQLKSGTASVVCLLNN FYPREAKVQWKVDNALQSGNSQESVTEQDSKDSTYSLSSTLTLSKAD YEKHKVYACEVTHQGLSSPVTKSFNRGEC* | 30 |

TABLE 2-continued

Heavy and Light Chain Sequences of IgG4
Nicotine-Binding Antibodies

| Antibody Chain | Amino Acid Sequence | SEQ ID NO: |
|---|---|---|
| 5H1-IgG4 Heavy | QVQLQESGPGLVKPSETLSLTCTVSGGSISRRNDYWAWIRQSPGKDL EWIGTISFSGSTFYNPSLKSRVTISADTFNNHFSLRLDAVAADTAV YYCARLSPFVGAAWWFDPWGPGTLVTVSS*ASTKGPSVFPLAPCSRST SESTAALGCLVKDYFPEPVTVSWNSGALTSGVHTFPAVLQSSGLYSL SSVVTVPSSSLGTKTYTCNVDHKPSNTKVDKRVESKYGPPCPPCPAP EFLGGPSVFLFPPKPKDTLMISRTPEVTCVVVDVSQEDPEVQFNWYV DGVEVHNAKTKPREEQFNSTYRVVSVLTVLHQDWLNGKEYKCKVSNK GLPSSIEKTISKAKGQPREPQVYTLPPSQEEMTKNQVSLTCLVKGFY PSDIAVEWESNGQPENNYKTTPPVLDSDGSFFLYSRLTVDKSRWQEG NFFSCSVMHEALHNHYTQKSLSLSLGK* | 31 |
| 5H1-IgG4 Light | EIVLTQSPGTLSLSPGERATLSCRASQSLSSNYLGWYQQKPGQAPRL LIYGASNRATGIPDRFSGSGSGTDFTLTISRLEPEDFGVYYCQRYGR SPPAITFGGGTKVEIK*RTVAAPSVFIFPPSDEQLKSGTASVVCLLNN FYPREAKVQWKVDNALQSGNSQESVTEQDSKDSTYSLSSTLTLSKAD YEKHKVYACEVTHQGLSSPVTKSFNRGEC* | 32 |
| 15A4-IgG4 Heavy | QLQLQESGPGLVKPSETLSLTCTASGGSITNNIDYWVWIRQPPGRGL EWIGTIYYSGSTFYNPSLKSRVTISVDTSNNQFSLNLNSMSAADTAV YYCARLRYYYDSNGYLPYWIDSWGQGTLVTVSS*ASTKGPSVFPLAPC SRSTSESTAALGCLVKDYFPEPVTVSWNSGALTSGVHTFPAVLQSSG LYSLSSVVTVPSSSLGTKTYTCNVDHKPSNTKVDKRVESKYGPPCPP CPAPEFLGGPSVFLFPPKPKDTLMISRTPEVTCVVVDVSQEDPEVQF NWYVDGVEVHNAKTKPREEQFNSTYRVVSVLTVLHQDWLNGKEYKCK VSNKGLPSSIEKTISKAKGQPREPQVYTLPPSQEEMTKNQVSLTCLV KGFYPSDIAVEWESNGQPENNYKTTPPVLDSDGSFFLYSRLTVDKSR WQEGNFFSCSVMHEALHNHYTQKSLSLSLGK* | 33 |
| 15A4-IgG4 Light | EIVLTQSPGTLSLSPGERATLSCRASQSISSSYLGWYQQKPGQAPRL LIYGASSRATGIPDRFSGSGSGTDFTLTISSLEPEDFAVYFCQLYRR SPPRLTFGGGTKVEIK*RTVAAPSVFIFPPSDEQLKSGTASVVCLLNN FYPREAKVQWKVDNALQSGNSQESVTEQDSKDSTYSLSSTLTLSKAD YEKHKVYACEVTLIQGLSSPVTKSFNRGEC* | 34 |
| 2E11-IgG4 Heavy | QLQLQESGPGLVKPSESLSLTCTVSGGSIISNDYYWAWIRQSPGKGL EWIGSINYRGSTFYSPLNSRVTTSVDTSKNQFFLKLTSVTAADTAM YFCTRLHGRYRGVRLAFDYWGQGTLVTVSS*ASTKGPSVFPLAPCSR STSESTAALGCLVKDYFPEPVTVSWNSGALTSGVHTFPAVLQSSGLY SLSSVVTVPSSSLGTKTYTCNVDHKPSNTKVDKRVESKYGPPCPPCP APEFLGGPSVFLFPPKPKDTLMISRTPEVTCVVVDVSQEDPEVQFNW YVDGVEVHNAKTKPREEQFNSTYRVVSVLTVLHQDWLNGKEYKCKVS NKGLPSSIEKTISKAKGQPREPQVYTLPPSQEEMTKNQVSLTCLVKG FYPSDIAVEWESNGQPENNYKTTPPVLDSDGSFFLYSRLTVDKSRWQ EGNFFSCSVMHEALHNHYTQKSLSLSLGK* | 35 |
| 2E11-IgG4 Light | DIQMTQSPSTLSASVGDIVTITCRASQSIGDWLAWYQQKPGKAPKLL IYKASNLESGVPSRFSGSGSGTEFTLTISSLQSDDFATYYCQQYDSY SVTFGQGTKVEIK*GTVAAPSVHFPPSDEQLKSGTASVFCLLNNFYPR EAKVQWKVDNALQSGNSQESVTEQDSKDSTYSLSSTLTLSKADYEKH KVYACEVTHQGLSSPVTKSFNRGEC* | 36 |
| 13F7-IgG4 Heavy | QVQLQEAGPGLVKPSETLSLTCTVSGGSINTRNYYWGWVRQPPGKGL EWIASVYYTGSTFYDPSLRSRVTISIDTPRNQFSLRVSSVDAGDMGV YYCVRLDGGYNNGYYYYGMDVWGQGTSVTVSS*ASTKGPSVFPLAPCS RSTSESTAALGCLVKDYFPEPVTVSWNSGALTSGVHTFPAVLQSSGL YSLSSVVTVPSSSLGTKTYTCNVDHKPSNTKVDKRVESKYGPPCPPC PAPEFLGGPSVFLFPPKPKDTLMISRTPEVTCVVVDVSQEDPEVQFN WYVDGVEVHNAKTKPREEQFNSTYRVVSVLTVLHQDWLNGKEYKCKV SNKGLPSSIEKTISKAKGQPREPQVYTLPPSQEEMTKNQVSLTCLVK GFYPSDIAVEWESNGQPENNYKTTPPVLDSDGSFFLYSRLTVDKSRW QEGNFFSCSVMHEALHNHYTQKSLSLSLGK* | 37 |
| 13F7-IgG4 Light | GVQMTQSPSTLSASVGERVTVTCRASRPISNWLSWYQQKPGRAPKLL IYGTSTLESGVPSRFSGSGSGTEFTLTITNLQPDDFATYYCQEHNLY TITFGPGTKVEIK*RTVAAPSVHFPPSDEQLKSGTASVFCLLNNFYPR EAKVQWKVDNALQSGNSQESVTEQDSKDSTYSLSSTLTLSKADYEKH KVYACEVTHQGLSSPVTKSFNRGEC* | 38 |
| 8H5-IgG4 Heavy | QLQLQESGPGLVKPSETLSLSCAVSGASIRSNTYYWGWIRQPPGRGL EWIGSISHRGDAHYSPSLKSPVTISVDTSKNEFSLKATSVTAADTAV YYCVSLAYSFSWNTYYFYGMDVWGHGITVTVSS*ASTKGPSVFPLAPC SRSTSESTAALGCLVKDYFPEPVTVSWNSGALTSGVHTFPAVLQSSG LYSLSSVVTVPSSSLGTKTYTCNVDHKPSNTKVDKRVESKYGPPCPP CPAPEFLGGPSVFLFPPKPKDTLMISRTPEVTCVVVDVSQEDPEVQF* | 39 |

TABLE 2-continued

Heavy and Light Chain Sequences of IgG4 Nicotine-Binding Antibodies

| Antibody Chain | Amino Acid Sequence | SEQ ID NO: |
|---|---|---|
| | *NWYVDGVEVHNAKTKPREEQFNSTYRVVSVLTVLHQDWLNGKEYKCK* *VSNKGLPSSIEKTISKAKGQPREPQVYTLPPSQEEMTKNQVSLTCLV* *KGFYPSDIAVEWESNGQPENNYKTTPPVLDSDGSFFLYSRLTVDKSR* *WQEG1VVFSCSVMHEALHNHYTQKSLSLSLGK* | |
| 8H5-IgG4 Light | DIVLTQSPGTLSLSPGEGATLSCRASQSVNSGYLAWYQQKPGQPPRL LVFAASSRATGIADRFRGSGSGTDFTLTITRLEPEDFAVYYCQLYGH SPARITFGQGTRLETK*RTVAAPSVFIFPPSDEQLKSGTASVVCLLNN* *FYPREAKVQWKVDNALQSGNSQESVTEQDSKDSTYSLSSTLTLSKAD* *YEKHKVYACEVTHQGLSSPVTKSFNRGEC* | 40 |

Heavy and light chain complementarity determining regions (CDRs) are shown in bold, underlined text.
CDR annotation was made according to IMGT numbering.
Constant regions are denoted in italicized, underlined text.

Also encompassed by the present disclosure are nicotine-binding antibodies and nicotine-binding fragments thereof comprising the same CDR sequences and/or the same framework region sequences and/or the same variable region sequences as one or more of the novel antibodies disclosed in Tables 1 and 2. In this regard, although the novel nicotine-binding antibodies disclosed in Tables 1 and 2 are IgG1 and IgG4 antibodies, respectively, other nicotine-binding antibodies within the scope of this disclosure may be IgG2, IgG3, IgA1, IgA2, IgE, IgH, or IgM, for example.

Human immunoglobulin IgG4 antibodies are good candidates for antibody-based therapy when, as here, reduced effector functions are desirable. However, IgG4 antibodies are dynamic molecules able to undergo a process known as Fab arm exchange (FAE). See, e.g., Labrijn et al., *Therapeutic IgG4 antibodies engage in Fab-arm exchange with endogenous human IgG4 in vivo*, NATURE BIOTECH 27(8): 767-71 (2009). This results in functionally monovalent, bispecific antibodies (bsAbs) with unknown specificity and hence, potentially, reduced therapeutic efficacy. FAE can be prevented by introducing a S228P mutation into the hinge region of the antibody. Thus, in some embodiments, a nicotine-binding antibody as disclosed herein comprises a S228P substitution. The novel antibodies disclosed in Table 2 comprise such a S228P substitution. In other embodiments, a nicotine-binding antibody as disclosed herein does not comprise a S228P substitution.

In some embodiments, a nicotine-binding antibody as disclosed herein comprises one or more additional or alternative substitutions, insertions, or deletions beyond the aforementioned S228P substitution. For example, in some embodiments, a nicotine-binding antibody of the present disclosure comprises heavy and light chains with at least about 85%, about 86%, about 87%, about 88%, about 89%, about 90%, about 91%, about 92%, about 93%, about 94%, about 95%, about 96%, about 97%, about 98%, about 99%, or about 100% identity to one or more of the heavy and light chain sequences disclosed in Tables 1 and 2, respectively. In some embodiments, a nicotine-binding antibody of the present disclosure comprises heavy and light chains with at least 85%, 86%, 87%, 88%, 89%, 90%, 91%, 92%, 93%, 94%, 95%, 96%, 97%, 98%, 99%, or 100% identity to one or more of the heavy and light chain sequences disclosed in Tables 1 and 2, respectively.

In some embodiments, the antibodies disclosed herein bind nicotine with a high affinity. As shown in Table 3 below, the novel antibodies of Tables 1 and 2 can bind to free S-nicotine with a $K_D$ in the nanomolar range. The $K_D$ values reported below were determined by Surface Plasmon Resonance Biosensor. Other methodology for determining binding affinity also can be used, such as equilibrium dialysis.

TABLE 3

Nicotine Binding Affinity

| Antibody | $K_D$ (nM) (S-Nicotine; 25° C.) |
|---|---|
| 8D1 | 5 |
| 12F5 | 29 |
| 7A8 | 30 |
| 5D1 | 30 |
| 5G4 | 31 |
| 5H1 | 37 |
| 15A4 | 40 |
| 2E11 | 61 |
| 13F7 | 62 |
| 8H5 | 67 |
| 5G4 IgG4 | 31 |
| 7A8 IgG4 | 30 |
| 12F5 IgG4 | 20 |
| 8D1 IgG4 | 5 |

Thus, in some embodiments, the nicotine-binding antibodies or fragments thereof disclosed herein have a $K_D$ of less than 100 nM. For example, in some embodiment, the nicotine-binding antibodies or fragments thereof have a $K_D$ for nicotine of less than about $1.5 \times 10^{-7}$, less than about $1.0 \times 10^{-7}$, less than about $0.5 \times 10^{-7}$, less than about $9.5 \times 10^{-8}$, less than about $9.0 \times 10^{-8}$, less than about $8.5 \times 10^{-8}$, less than about $8.0 \times 10^{-8}$, less than about $7.5 \times 10^{-8}$, less than about $7.0 \times 10^{-8}$, less than about $6.5 \times 10^{-8}$, less than about $6.0 \times 10^{-8}$, less than about $5.5 \times 10^{-8}$, less than about $5.0 \times 10^{-8}$, less than about $4.5 \times 10^{-8}$, less than about $4.0 \times 10^{-8}$, less than about $3.5 \times 10^{-8}$, less than about $3.0 \times 10^{-8}$, less than about $2.5 \times 10^{-8}$, less than about $2.0 \times 10^{-8}$, less than about $1.5 \times 10^{-8}$, less than about $1.0 \times 10^{-8}$, less than about $0.5 \times 10^{-8}$, less than about $9.5 \times 10^{-9}$, less than about $9.0 \times 10^{-9}$, less than about $8.5 \times 10^{-9}$, less than about $8.0 \times 10^{-9}$, less than about $7.5 \times 10^{-9}$, less than about $7.0 \times 10^{-9}$, less than about $6.5 \times 10^{-9}$, less than about $6.0 \times 10^{-9}$, less than about $5.5 \times 10^{-9}$, less than about $5.0 \times 10^{-9}$, less than about $4.5 \times 10^{-9}$, less than about $4.0 \times 10^{-9}$, less than about $3.5 \times 10^{-9}$, less than about $3.0 \times 10^{-9}$, less than about $2.5 \times 10^{-9}$, less than about $2.0 \times 10^{-9}$, less than about $1.5 \times 10^{-9}$, less than about $1.0\times10^{-9}$, less than about $0.5\times10^{-9}$, less than about $9.5\times10^{-10}$, less than about $9.0\times10^{-10}$, less than about $8.5\times10^{-10}$, or less than about $8.0\times10^{-10}$ M. In some embodiment, the nicotine-binding antibodies or fragments thereof have a $K_D$ for nicotine of less than $1.5\times10^{-7}$, less than $1.0\times10^{-7}$, less than $0.5\times10^{-7}$, less than $9.5\times10^{-8}$, less than $9.0\times10^{-8}$, less than $8.5\times10^{-8}$, less than $8.0\times10^{-8}$, less than $7.5\times10^{-8}$, less than $7.0\times10^{-8}$, less than $6.5\times10^{-8}$, less than $6.0\times10^{-8}$, less than $5.5\times10^{-8}$, less than $5.0\times10^{-8}$, less than $4.5\times10^{-8}$, less than $4.0\times10^{-8}$, less than $3.5\times10^{-8}$, less than $3.0\times10^{-8}$, less than $2.5\times10^{-8}$, less than $2.0\times10^{-8}$, less than $1.5\times10^{-8}$, less than $1.0\times10^{-8}$, less than $0.5\times10^{-8}$, less than $9.5\times10^{-9}$, less than $9.0\times10^{-9}$, less than $8.5\times10^{-9}$, less than $8.0\times10^{-9}$, less than $7.5\times10^{-9}$, less than $7.0\times10^{-9}$, less than $6.5\times10^{-9}$, less than $6.0\times10^{-9}$, less than $5.5\times10^{-9}$, less than $5.0\times10^{-9}$, less than $4.5\times10^{-9}$, less than $4.0\times10^{-9}$, less than $3.5\times10^{-9}$, less than $3.0\times10^{-9}$, less than $2.5\times10^{-9}$, less than $2.0\times10^{-9}$, less than $1.5\times10^{-9}$, less than $1.0\times10^{-9}$, less than $0.5\times10^{-9}$, less than $9.5\times10^{-10}$, less than $9.0\times10^{-10}$, less than $8.5\times10^{-10}$, or less than $8.0\times10^{-10}$ M.

In some embodiments, the disclosed nicotine-binding antibodies or fragments thereof have a $K_D$ for nicotine between 100 nM and 0.01 nM, between 90 nM and 0.05 nM, between 80 nM and 0.1 nM, between 70 nM and 0.5 nM, between 70 nM and 1.0 nM, between 60 nM and 30 nM, or any value in between. For example, in some embodiments, the disclosed nicotine-binding antibodies or fragments thereof have a $K_D$ for nicotine of less than 100 nM, less than 60 nM, less than 30 nM, less than 10 nM, less than 5 nM, or less than 1 nM.

Nicotine has two enantiomers: S-(−)-nicotine and R-(+)-nicotine, with the S-enantiomer known to be the most physiologically active. In some embodiments, the disclosed nicotine-binding antibodies exhibit selectivity for one enantiomer over the other. For instance, in some embodiments, a nicotine-binding antibody selectively binds to S-(−)-nicotine with a higher affinity than it binds to R-(+)-nicotine, while in some embodiments a nicotine-binding antibody may bind S-(−)-nicotine and substantially not bind to R-(+)-nicotine. For example, 8D1-IgG4 and 12F5-IgG4 preferentially bind to S-(−)-nicotine. In this regard, 8D1-IgG4 has a $K_D$ for R-(+)-nicotine of 92 nM and 12F5-IgG4 has a $K_D$ for R-(+)-nicotine of 1.2 µM. These disclosed antibodies exhibit greater binding affinity and selectivity for S-(−)-nicotine than has previously been reported for previously described nicotine-binding antibodies, such as the Nic12 mAb, which is disclosed in U.S. Pat. No. 8,344,111 and Tars et al., J. Mol. Bio., 415: 118-127 (2012).

Alternatively, in some embodiments, a nicotine-binding antibody may selectively bind to R-(+)-nicotine with a higher affinity than it binds to S-(−)-nicotine, while in some embodiments a nicotine-binding antibody may bind to R-(+)-nicotine and substantially not bind to S-(−)-nicotine.

In some embodiments, a nicotine-binding antibody may bind to both enantiomers of nicotine with comparable affinity.

In some embodiments, the disclosed nicotine-binding antibodies have a strong binding affinity for nicotine (one or both enantiomers) and a comparatively weak binding affinity for other molecules that may be present in a subject being treated, including molecules that are chemically- and/or structurally-related to nicotine, metabolites or byproducts of nicotine (e.g., cotinine), molecules that are ligands of or that bind to nicotinic receptors, drugs (e.g., small molecule drugs) used to aid smoking cessation (e.g., bupropion, varenicline, and cytisine) and/or treat nicotine addiction and/or nicotine toxicity, and/or other endogenous or exogenous molecules that may be present in a subject's blood, including neurotransmitters and other molecules that may be administered to diagnose or treat a condition in the subject or to maintain or support normal physiology. In other words, in some embodiments, the disclosed nicotine-binding antibodies do not cross-react with molecules that are not nicotine, i.e., "off-target compounds".

The percent of cross reactivity (% cross reactivity to mAb ($IC_{50, Nicotine}/IC_{50, Compound X}$ 100%)) of the disclosed antibodies against several exemplary molecules is shown in Table 4 below. Of these, cotinine, nicotinamide, B-nicotinamide adenine dinucleotide, and nornicotine are nicotine-related molecules; bupropion, varenicline and cytisine are smoking-cessation drugs, and acetylcholine chloride, 3-hydroxytyramine (dopamine), serotonin, and norepinephrine are neurotransmitters. A cross-reactivity of less than 0.1%, less than 0.05%, less than 0.01%, or less than 0.005%, or less than 0.001%, or less than 0.0005%, or less than 0.0001% is considered to be substantially not cross-reactive.

TABLE 4

Cross Reactivity of Exemplary Antibodies

| Compound | 8D1 | 12F5 | 7A8 | 5G4 |
|---|---|---|---|---|
| S-Nicotine affinity $K_D$ (nM) | 5 | 29 | 30 | 31 |
| S-Nicotine | 100 | 100 | 100 | 100 |
| Cotinine | NCR* | NCR | 0.0938 | 0.0352 |
| Acetylcholine Chloride | NCR | NCR | NCR | NCR |
| Nicotinamide | NCR | NCR | NCR | 0.0004 |
| 3-Hydroxy-tyramineHCl (Dopamine HCl) | 0.0003 | NCR | NCR | NCR |
| Serotonin Hydrochloride | NCR | NCR | NCR | NCR |
| (+/−)-Norepinephrine (+)-Bitartrate Salt | 0.0005 | 0.0296 | 0.0020 | 0.0015 |
| Nornicotine | NCR | NCR | 0.0558 | 0.1971 |
| Bupropion | NCR | NCR | NCR | 0.0106 |
| Cytisine | 0.0001 | NCR | NCR | NCR |
| Varenicline tartrate | 0.0002 | NCR | NCR | 0.0018 |
| B-Nicotinamide Adenine Dinucleotide | 0.0002 | NCR | 0.0036 | 0.0037 |

*NCR = no cross reactivity detected
Value are shown as percent of cross reactivity, which was calculated using the equation: ($IC_{50, Nicotine}/IC_{50, Compound}$ × 100%)

Binding affinity for nicotine over cotinine is particularly advantageous because cotinine is the major human metabolite of nicotine and has a longer half-life than nicotine, so it often accumulates at high concentrations relative to nicotine in smokers and other individuals who consume nicotine-based products. Indeed, this is a reason that cotinine is used for testing to determine if someone is a smoker. Given the high levels of circulating cotinine found in individuals that consume nicotine-based products (e.g., cigarettes, e-cigarettes, smokeless tobacco, etc.), a nicotine-binding antibody that also exhibits substantial binding affinity for cotinine would be less effective for treating nicotine poisoning or facilitating smoking cessation, since the antibody would bind to cotinine as well as nicotine, limiting its efficacy at binding (and sequestering) nicotine. Thus, the binding selectivity of the specific antibodies disclosed herein is a significant advantageous property that supports their efficacy in clinical applications.

Binding affinity for nicotine over bupropion, varenicline and/or cytisine also is advantageous because those drugs are commonly used for smoking cessation. The binding selectivity of the specific antibodies disclosed herein and their lack of binding affinity for bupropion, varenicline and cytisine indicates that they could be used in combination with bupropion, varenicline and/or cysteine, since the antibodies would not bind those drugs. Thus, in some embodiments, the methods disclosed herein include administering an antibody as disclosed herein that does not exhibit binding affinity to bupropion, varenicline and/or cytisine (such as any of the antibodies set forth in the Table 4) in a combination therapy with a smoking cessation drug (such as bupropion, varenicline and/or cytisine), wherein the antibodies and drugs may be administered substantially simultaneously or sequentially in any order. Such embodiments may be particularly advantageous in methods for facilitating smoking cessation, quitting smoking (or quitting using other nicotine products), maintaining abstinence from smoking (or use of other nicotine products), or decreasing consumption of nicotine products.

The data shown in Table 4 also indicate that the disclosed antibodies do not bind to neurotransmitters. This type of binding selectivity is advantageous because it indicates that the disclosed antibodies are not likely to interfere with normal brain physiology/pharmacology.

In some embodiments, the nicotine-binding antibody or fragment is a long-acting variant that has been modified in order to extend its half-life in vivo (after administration). Various techniques are known in the art for extending the circulating half-life of peptides, such as antibodies. For example, in some embodiments the antibody carries mutations in the Fc region with enhanced FcRn-mediated recycling such as "YTE" (M252Y/S254T/T256E), see e.g., Dall'Acqua et al., J Biol Chem., 281:23514-24 (2006), or "Xtend" Fc domain mutations from Xencor (US 2014/0056879 A1). In other embodiments, the antibody or fragment thereof is conjugated to polyethylene glycol (PEG; i.e., the antibody is PEGylated) or a similar polymer that prolongs half-life. In some embodiments, the antibody is fused to an albumin-binding peptide, an albumin-binding protein domain, human serum albumin, or an inert polypeptide. Exemplary inert polypeptides that have been used to increase the circulating half-life of peptides include, but are not limited to, XTEN® (also known as recombinant PEG or "rPEG"), a homo-amino acid polymer (HAP; HAPylation), a proline-alanine serine polymer (PAS; PASylation), or an elastin-like peptide (ELP; ELPylation). As used herein, "fused to" includes genetic fusion, directly or through a linker, resulting in a single polypeptide containing multiple domains, unless otherwise specified.

The nicotine-binding antibody or a nicotine-binding fragment thereof can be formulated in a pharmaceutical composition suitable for administration to the target subject by the intended route of administration, as discussed in more detail below.

IV. Pharmaceutical Compositions

Pharmaceutical compositions suitable for use in the methods described herein can include the disclosed nicotine-binding antibodies or fragments thereof and a pharmaceutically acceptable carrier or diluent.

The composition may be formulated for intravenous, subcutaneous, intraperitoneal, intramuscular, oral, nasal, pulmonary, ocular, vaginal, or rectal administration. In some embodiments, nicotine-binding antibodies are formulated for intravenous, subcutaneous, intraperitoneal, or intramuscular administration, such as in a solution, suspension, emulsion, liposome formulation, etc. The pharmaceutical composition can be formulated to be an immediate-release composition, sustained-release composition, delayed-release composition, etc., using techniques known in the art.

Pharmacologically acceptable carriers for various dosage forms are known in the art. For example, excipients, lubricants, binders, and disintegrants for solid preparations are known; solvents, solubilizing agents, suspending agents, isotonicity agents, buffers, and soothing agents for liquid preparations are known. In some embodiments, the pharmaceutical compositions include one or more additional components, such as one or more preservatives, antioxidants, colorants, sweetening/flavoring agents, adsorbing agents, wetting agents and the like.

In some embodiments, the disclosed nicotine-binding antibodies or fragments thereof may be formulated for administration by injection or infusion. In some embodiments, the nicotine-binding antibody or fragment thereof is formulated for administration by a non-oral route since nicotine poisoning may induce vomiting, thus limiting the effectiveness of oral administration for that particular indication.

V. Methods of Treating Nicotine Poisoning

As noted above, in some aspects the methods of treating nicotine overdose or nicotine poisoning described herein comprise administering to a mammalian subject in need thereof a nicotine-binding antibody or nicotine-binding fragment thereof as disclosed herein, or a pharmaceutical composition comprising the same. In some embodiments, the methods comprise administering a nicotine-binding antibody or nicotine-binding fragment thereof to a subject that has ingested or consumed a toxic amount of nicotine. In some embodiments, the methods may comprise administering both a nicotine-binding antibody or nicotine-binding fragment thereof and another compound that is useful for treating nicotine poisoning, such as activated charcoal. In such embodiments, the antibody or fragment and the second compound (e.g., activated charcoal) can be administered sequentially or simultaneously, from the same or different compositions. Thus, the treatment may include administering activated charcoal and/or other supportive treatments to address the symptoms and/or effects of nicotine poisoning.

In some embodiments, the therapeutically effective amount of the nicotine-binding antibody or fragment thereof is effective to reduce plasma levels of nicotine, and/or to reduce levels of nicotine localized in the brain, and/or to reduce, ameliorate, or eliminate one or more symptoms or effects of nicotine poisoning or overdose. The specific amount administered may depend on one or more of the age and/or weight of the subject, the amount of nicotine believed to have been ingested, and/or the subject's plasma level of nicotine at the time of treatment, and/or the subject's brain level of nicotine at the time of treatment.

In some embodiments, the nicotine-binding antibody is administered at a dose of from about 50 to about 1000 mg/kg, about 150 mg/kg to about 850 mg/kg, about 250 mg/kg to about 750 mg/kg, about 350 mg/kg to about 650 mg/kg, or about 450 mg/kg to about 550 mg/kg. In some embodiments, the nicotine-binding antibody is administered at a dose of from 50 to 1000 mg/kg, 150 mg/kg to 850 mg/kg, 250 mg/kg to 750 mg/kg, 350 mg/kg to 650 mg/kg, or 450 mg/kg to 550 mg/kg. In some embodiments, the nicotine-binding antibody is administered at a dose of about 50 mg/kg, about 100 mg/kg, about 150 mg/kg, about 200 mg/kg, about 250 mg/kg, about 300 mg/kg, about 350 mg/kg, about 400 mg/kg, about 450 mg/kg, about 500 mg/kg, about 550 mg/kg, about 600, about 650 mg/kg, about 700 mg/kg, about 750 mg/kg, about 800 mg/kg, about 850 mg/kg, about 900 mg/kg, about 950 mg/kg, or about 1000 mg/kg. In some embodiments, the nicotine-binding antibody is administered at a dose of 50 mg/kg, 100 mg/kg, 150 mg/kg, 200 mg/kg, 250 mg/kg, 300 mg/kg, 350 mg/kg, 400 mg/kg, 450 mg/kg, 500 mg/kg, 550 mg/kg, 600, 650 mg/kg, 700 mg/kg, 750 mg/kg, 800 mg/kg, 850 mg/kg, 900 mg/kg, 950 mg/kg, or 1000 mg/kg. In some embodiments, the nicotine-binding antibody is administered at a dose of about 3000 mg, about 3500 mg, about 4000 mg, about 4500 mg, about 5000 mg, about 5500 mg, about 6000, about 6500 mg, about 7000 mg, about 7500 mg, about 8000 mg, about 8500 mg, about 9000 mg, about 9500 mg, about 10000 mg, about 10500 mg, about 11000 mg, about 11500 mg, or about 12000 mg. In some embodiments, the nicotine-binding antibody is administered at a dose of 3000 mg, 3500 mg, 4000 mg, 4500 mg, 5000 mg, 5500 mg, 6000, 6500 mg, 7000 mg, 7500 mg, 8000 mg, 8500 mg, 9000 mg, 9500 mg, 10000 mg, 10500 mg, 11000 mg, 11500 mg, or 12000 mg. In some embodiments, the nicotine-binding antibody is administered at a dose of up to about 10 g. When other antibody-related constructs are used, such as antibody fragments, they can be used at comparable doses adjusted for their different molecular weights and/or binding affinities. For example, the dose of a fragment can be chosen to achieve comparable $C_{max}$ and/or AUC parameters as the corresponding full-length antibody, or to achieve binding of a comparable amount of nicotine.

In some embodiments, the nicotine-binding antibody is administered as a dose based on the molar ratio of antibody to nicotine. For instance, in some embodiments, the ratio of antibody:nicotine is 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10. The disclosed nicotine-binding antibodies possess two nicotine binding sites per antibody, while a Fab of the disclosed nicotine-binding antibodies may only have one nicotine binding site. Accordingly, the dose may be adjusted based on the number of nicotine binding sites per molecule. For example, if one assumes that the MW for a full length antibody is 150 KD and 50 KD for a Fab, then an "equimolar dose amount" adjusted for the number of nicotine binding sites would be equivalent to a 50% higher dose amount (in mg/kg) for the full length antibody versus the Fab. These amounts are based on the assumption that the pharmacokinetic profile is substantially the same between the full-length antibody and the Fab; if that is not the case, those of ordinary skill in the art can adjust the amounts as needed in the event that the pharmacokinetic profiles are different.

In some embodiments, the method comprises administering a single dose of a pharmaceutical composition comprising a nicotine-binding antibody or nicotine-binding fragment thereof, or a single dose of a pharmaceutical composition comprising a nicotine-binding antibody or nicotine-binding fragment thereof and another compound. In other embodiments, the method comprises administering repeated doses of the pharmaceutical composition(s) until the symptoms or effects of nicotine poisoning or nicotine overdose are reduced, ameliorated, or eliminated. For instance, a subject with nicotine poisoning or overdose may be evaluated for the presence and/or severity of signs and symptoms associated with nicotine poisoning, including, but not limited to, seizures, coma, shortness of breath, and increased heart rate, and treated with one or more pharmaceutical composition(s) as described herein until one or more of the signs/symptoms is reduced, ameliorated, or eliminated after treatment. In some embodiments, samples are taken to monitor nicotine levels in the subject's plasma or brain. In some embodiments, treatment is repeated with additional doses of the pharmaceutical composition(s) if signs/symptoms/effects persist and/or if nicotine plasma or brain levels remain elevated, and can be continued (repeated) until one or more symptoms or effects of nicotine poisoning or nicotine overdose are reduced, ameliorated, or eliminated, and/or until plasma levels and/or brain levels are reduced.

In some embodiments, treating a subject with nicotine poisoning or overdose may comprise extracorporeal detoxification of the subject's blood. For instance, the disclosed nicotine-binding antibodies or nicotine-binding fragments thereof can be attached to an affinity column through which the subject's blood can be circulated. This process can remove circulating nicotine from the subject's blood.

VI. Methods of Aiding in Smoking Cessation

As noted above, the antibodies described herein are useful in methods of treating nicotine addiction and/or facilitating smoking cessation (or the cessation of use of other nicotine products) in a mammalian subject in need thereof. In some embodiments, the subject is a human subject addicted to nicotine or desiring to quit smoking (or quit using other nicotine products) or maintain abstinence from smoking or consumption of other nicotine products.

As disclosed in the Examples section below, in some embodiments, the disclosed nicotine-binding antibodies or nicotine-binding fragments thereof attenuate nicotine's effects and do not induce withdrawal symptoms at predicted therapeutic doses, and have been demonstrated to aid in smoking cessation and the maintenance of abstinence in pre-clinical studies. The results have been noteworthy, as the negative affective consequences of early nicotine withdrawal are recognized as significant contributors to relapse to tobacco smoking during quit attempts, and the maintenance of compulsive nicotine use. In addition, the enhancement by nicotine of the reward value of other environmental rewarding stimuli is considered critical in the maintenance of nicotine dependence. Thus, blockade of nicotine-induced reward enhancement without inducing strong withdrawal effects are desirable properties of nicotine-binding antibodies and nicotine-binding fragments thereof as a putative anti-smoking medications that may play an important role in preventing relapse within the quit process and in the maintenance of abstinence.

Furthermore, the ligand-binding approach of the disclosed nicotine-binding antibodies and nicotine-binding fragments thereof is complementary to the pharmacodynamic mechanisms of non-nicotine pharmacotherapies, such as varenicline and bupropion. Without being bound by theory, the mechanism of the disclosed antibodies and fragments may be that when a smoker quits and then slips or relapses, the attenuation of nicotine's reinforcing effects helps to prevent resumption of regular smoking. Further, in clinical trials, a greater number of quit attempts per subject were made in the high antibody group, as compared to placebo, consistent with this postulated relapse-prevention mechanism.

The methods generally involve administering a therapeutically effective amount of a nicotine-binding antibody or nicotine-binding fragment thereof as described herein (or a pharmaceutical composition comprising the same) to the subject. However, in some embodiments, the methods comprise administering a nucleic acid encoding the nicotine-binding antibody in a construct that expresses the antibody in vivo. For example, in such embodiments, the nucleic acid can be provided in a suitable vector, such as an adeno-associated virus (AAV) gene transfer vector. Other exemplary vectors that are suitable for use in such methods are known in the art. See, e.g., Lukashev and Zamyatnin, *Biochem.*, 81(7): 700-8 (2016)). Exemplary vectors may include one or more enhancers (e.g., a cytomegalovirus (CMV) enhancer), promoters (e.g., chicken (3-actin promoter), and/or other elements enhancing the properties of the expression cassette. Methods of making suitable vectors and general methods of using expression vectors in vivo are known in the art. See, e.g., (see Hicks et al., *Sci. Transl. Med.*, 4(140): 140ra87 (2012)).

In some embodiments, a subject in need of treatment for nicotine addiction or facilitation of smoking cessation is a human subject who consumes nicotine products, such as smoking tobacco, chewing tobacco, electronic cigarettes, and/or other nicotine delivery devices. Such a subject may or may not be physically addicted to nicotine and/or psychologically addicted to consuming nicotine products. Typical subjects in need of smoking cessation treatment smoke or use tobacco or other nicotine products daily, such as smoking at least 1 or more cigarettes a day, such as at least about 5, at least about 10, at least about 15, at least about 20 or more, cigarettes per day, including fewer than 10, 10-20, 20-30, 30-40, or 40 or more (or the equivalent use of other tobacco or nicotine products).

In some embodiments, a therapeutically effective amount of a nicotine-binding antibody is an amount effective to reduce plasma levels of nicotine, to reduce levels of nicotine localized in the brain, or both.

Nicotine exerts many of its significant effects after it crosses the blood brain barrier. In some embodiments, the methods and uses described herein reduce or prevent nicotine from crossing the blood-brain-barrier. Thus, in some embodiments, administration of a nicotine-binding antibody as described herein binds up or sequesters nicotine circulating in the bloodstream of the subject, thereby reducing or preventing the nicotine from crossing the blood-brain-barrier. Thus, in some embodiments, the methods described herein reduce or prevent the physiological and psychological effects of nicotine that originate in the brain. Because the subject will experience a lessening or cessation of these effects, he/she will lose the desire to consume nicotine products. Additionally or alternatively, the disclosed nicotine-binding antibody may exert an effect by affecting the ability of nicotine to stimulate the peripheral nervous system.

The specific amount of a nicotine-binding antibody or nicotine-binding fragment thereof that is administered may depend on one or more of the age and/or weight of the subject, the amount of nicotine routinely consumed (e.g., smoked, chewed. or inhaled), and/or the level of nicotine in the subject's brain or plasma at the time of treatment. For instance, in some embodiments, the nicotine-binding antibody is administered at a dose of from about 50 to about 1000 mg/kg, about 150 mg/kg to about 850 mg/kg, about 250 mg/kg to about 750 mg/kg, about 350 mg/kg to about 650 mg/kg, or about 450 mg/kg to about 550 mg/kg. In some embodiments, the nicotine-binding antibody is administered at a dose of from 50 to 1000 mg/kg, 150 mg/kg to 850 mg/kg, 250 mg/kg to 750 mg/kg, 350 mg/kg to 650 mg/kg, or 450 mg/kg to 550 mg/kg. In some embodiments, the nicotine-binding antibody is administered at a dose of about 50 mg/kg, about 100 mg/kg, about 150 mg/kg, about 200 mg/kg, about 250 mg/kg, about 300 mg/kg, about 350 mg/kg, about 400 mg/kg, about 450 mg/kg, about 500 mg/kg, about 550 mg/kg, about 600, about 650 mg/kg, about 700 mg/kg, about 750 mg/kg, about 800 mg/kg, about 850 mg/kg, about 900 mg/kg, about 950 mg/kg, or about 1000 mg/kg. In some embodiments, the nicotine-binding antibody is administered at a dose of 50 mg/kg, 100 mg/kg, 150 mg/kg, 200 mg/kg, 250 mg/kg, 300 mg/kg, 350 mg/kg, 400 mg/kg, 450 mg/kg, 500 mg/kg, 550 mg/kg, 600, 650 mg/kg, 700 mg/kg, 750 mg/kg, 800 mg/kg, 850 mg/kg, 900 mg/kg, 950 mg/kg, or 1000 mg/kg. In some embodiments, the nicotine-binding antibody is administered at a dose of about 3000 mg, about 3500 mg, about 4000 mg, about 4500 mg, about 5000 mg, about 5500 mg, about 6000, about 6500 mg, about 7000 mg, about 7500 mg, about 8000 mg, about 8500 mg, about 9000 mg, about 9500 mg, about 10000 mg, about 10500 mg, about 11000 mg, about 11500 mg, or about 12000 mg. In some embodiments, the nicotine-binding antibody is administered at a dose of 3000 mg, 3500 mg, 4000 mg, 4500 mg, 5000 mg, 5500 mg, 6000, 6500 mg, 7000 mg, 7500 mg, 8000 mg, 8500 mg, 9000 mg, 9500 mg, 10000 mg, 10500 mg, 11000 mg, 11500 mg, or 12000 mg. In some embodiments, the nicotine-binding antibody is administered at a dose of up to about 10 g. When other antibody-related constructs are used, such as antibody fragments, they can be used at comparable doses adjusted for their different molecular weights and/or binding affinities. For example, the dose of a fragment can be chosen to achieve comparable Cmax and/or AUC parameters as the corresponding full-length antibody, or to achieve binding of a comparable amount of nicotine.

In some embodiments, the methods comprise administering a single dose of a nicotine-binding antibody(s) or nicotine-binding fragment(s) thereof (or composition comprising the same). In some embodiments, the method comprises administering repeated doses, such as for a predetermined period of time of until the symptoms or effects of nicotine addiction are reduced, ameliorated, or eliminated or until the subject has ceased smoking or otherwise consuming nicotine. In some embodiments, treatment is repeated with additional doses of the variant(s) if signs/symptoms/effects persist or if the subject continues to have nicotine cravings or experiences them anew.

In some embodiments, the methods comprise administering a nicotine-binding antibody(s) or nicotine-binding fragment(s) thereof (or composition comprising the same) three or more times a day, twice a day, or once a day. In some embodiments, the methods comprise administering a nicotine-binding antibody(s) or nicotine-binding fragment(s) thereof (or composition comprising the same) once every other day, three times a week, twice a week, once a week, once every other week, once every three weeks, once a month, or less frequently. In such embodiments, the nicotine-degrading enzyme variant may be a long-acting nicotine-binding antibody as described above.

In some embodiments, treatment may continue for 1, 2, 3, 4, 5, 6, 7, 8, 9, 10, 11, 12, 13, 14, 15, 16, 17, 18, 19, 20, or 21 or more days; 1, 2, 3, 4, 5, 6, 7, 8, 9, 10, 11, 12, 13, 14, 15, 16, 17, or 18 or weeks months; or 1, 2, 3, 4, 5, 6, 7, 8, 9, 10, 11, or 12 or more months; or 1, 2, or 3 or more years or until the subject no long experiences nicotine cravings or other nicotine withdrawal symptoms, or has ceased smoking or using other tobacco products.

As noted above, in some embodiments, the methods disclosed herein include administering an antibody as disclosed herein that does not exhibit binding affinity to smoking cessation drug (such as bupropion, varenicline and/or cytisine) in a combination therapy with a smoking cessation drug (such as bupropion, varenicline and/or cytisine, respectively), wherein the antibodies and drugs may be administered substantially simultaneously or sequentially in any order. Such embodiments may be particularly advantageous in methods for facilitating smoking cessation, quitting smoking (or quitting using other nicotine products), maintaining abstinence from smoking (or use of other nicotine products), or decreasing consumption of nicotine products. One skilled in the art will readily appreciate that the present disclosure is well adapted to carry out the objects and obtain the ends and advantages mentioned, as well as those inherent therein. Modifications therein and other uses will occur to those skilled in the art. These modifications are encompassed within the spirit of the disclosure.

The following examples illustrate the invention. It should be understood, however, that the invention is not to be limited to the specific conditions or details described in these examples. All printed publications referenced herein are specifically incorporated by reference.

EXAMPLES

Example 1—Treatment of a Pediatric Patient with an Anti-Nicotine Antibody

This example illustrates methods using anti-nicotine antibodies in the treatment of nicotine poisoning or nicotine overdose.

A child known to have or suspected of having ingested nicotine is administered a therapeutically effective amount of a pharmaceutical composition comprising a nicotine-binding antibody, by intravenous, intramuscular, or subcutaneous injection. The child is evaluated for the presence and/or severity of signs and symptoms associated with nicotine poisoning, including, but not limited to, seizures, coma, shortness of breath, and increased heart rate, and the child is treated until one or more signs/symptoms is reduced, ameliorated, or eliminated. Optionally, another dose of the pharmaceutical composition is administered if signs/symptoms persist and/or if nicotine plasma levels remain elevated.

Example 2—Treating Nicotine Addiction and/or Facilitating Smoking Cessation

This example illustrates methods of using a variant as described herein to treat nicotine addiction and/or facilitate smoking cessation in a human adult.

An adult human subject who regularly smokes cigarettes but wishes to quit is administered a therapeutically effective amount of a pharmaceutical compositions comprising a nicotine-binding antibody (e.g., the antibodies disclosed in Tables 1 and 2, or a long-acting version thereof) by intravenous, intramuscular, or subcutaneous injection. The subject is evaluated for levels of nicotine circulating in plasma, as well as for the presence and/or severity of signs and symptoms associated with nicotine withdrawal, such as headache, irritability, anxiety, and sleeplessness, as well as the number of cigarettes smoked in a given day. The subject is treated with repeated administrations of the antibody until levels of nicotine circulating in plasma reach a target (reduced) level, and/or until one or more signs/symptoms of nicotine withdrawal are reduced, ameliorated, or eliminated, and/or until the subject has reduced the level of consumption of nicotine products (e.g., is smoking fewer cigarettes per day), and/or until the subject has ceased consumption of nicotine products (e.g., has quit smoking).

Example 3—In Vivo Kinetic Studies

A single dose nicotine pharmacokinetic study was carried out in rats (N=8). Rats were pre-treated with 20 mg/kg of 5G4 IgG4, 7A8 IgG4, 12F5 IgG4, or 8D1 IgG4, and then 0.03 mg/kg of nicotine was administered intravenously. The nicotine dose was administered in less than 10 seconds (it takes roughly 10 minutes to smoke a cigarette. Three minutes later, animals were sacrificed and the amount of nicotine in their blood and brains was quantified.

Figure 1B:
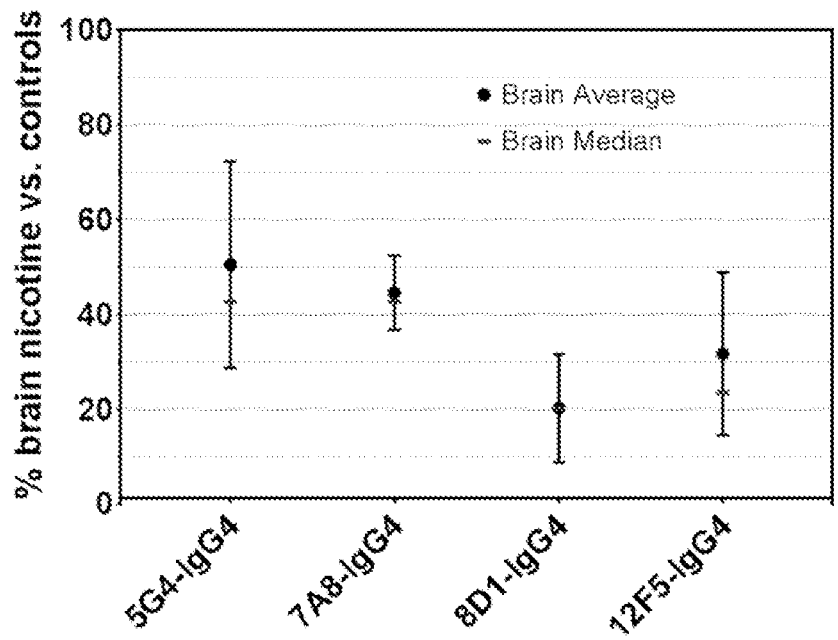

FIGS. 1A and 1B show the blood and brain concentrations, respectively, as a percent of levels in control rats not pre-treated with antibody. Each antibody reduced the levels of nicotine in the brain compared to control animals that were not pre-treated with antibody. For example, the 8D1 IgG4 antibody produced an 80% decrease in the level of nicotine localized in the brain.

Example 4—In Vivo Dose-Response Studies

A single dose nicotine dose-response study was carried out in rats (N=8). Rats were used since their nicotine metabolism is generally similar to humans in rate and range of metabolites. Rats were pre-treated with 10, 20, or 40 mg/kg of 12F5 IgG4 or 8D1 IgG4. Subsequently, 0.03 mg/kg of nicotine was administered intravenously in less than 10 seconds. Three minutes later, the animals were sacrificed and the amount of nicotine in their serum and brains was quantified.

Figure 2A:
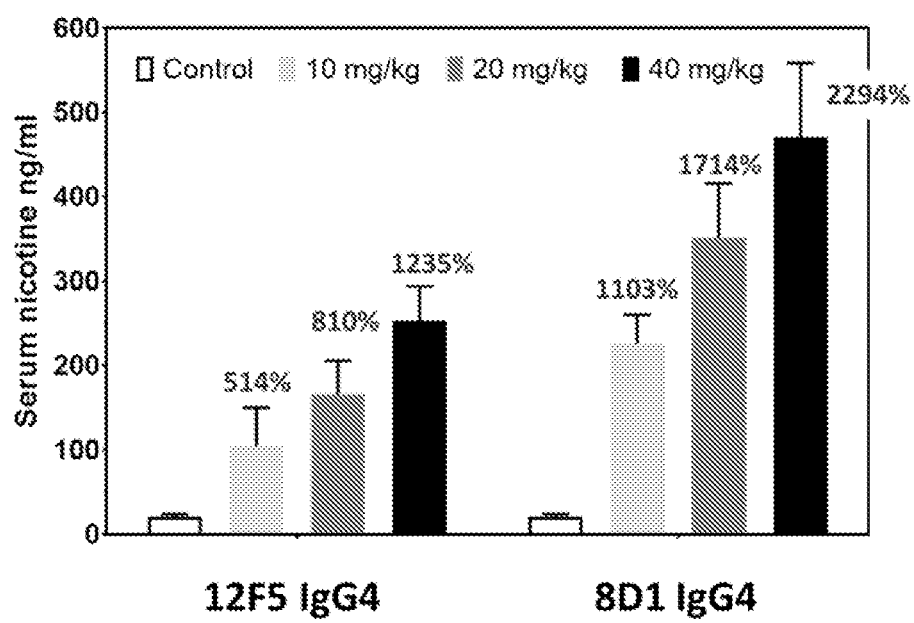
FIGS. 2A and 2B show the results of a dose response study of exemplary nicotine-binding antibodies in rats.
Figure 2B:
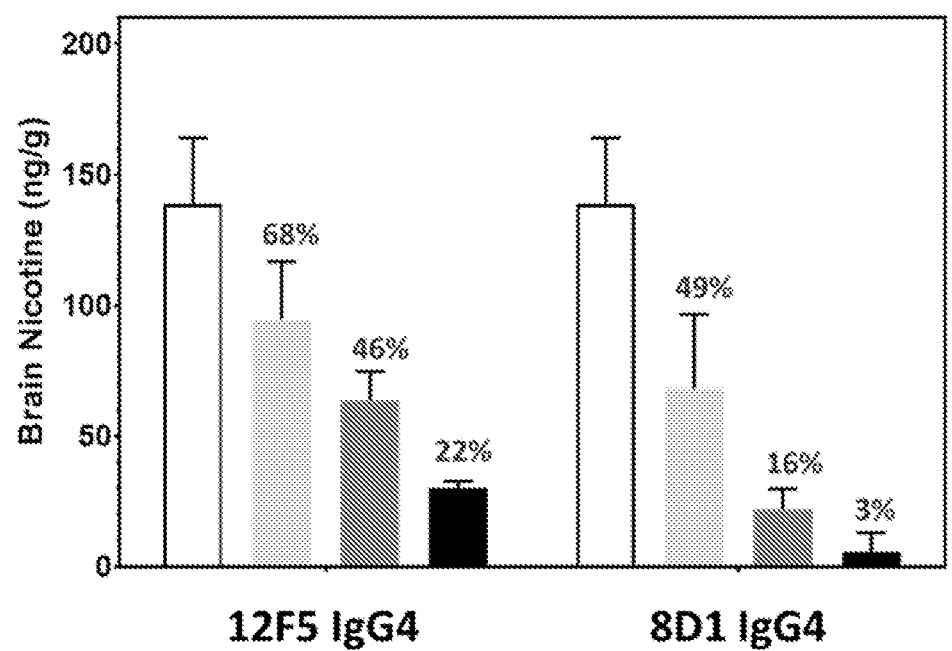
Figure 3A:
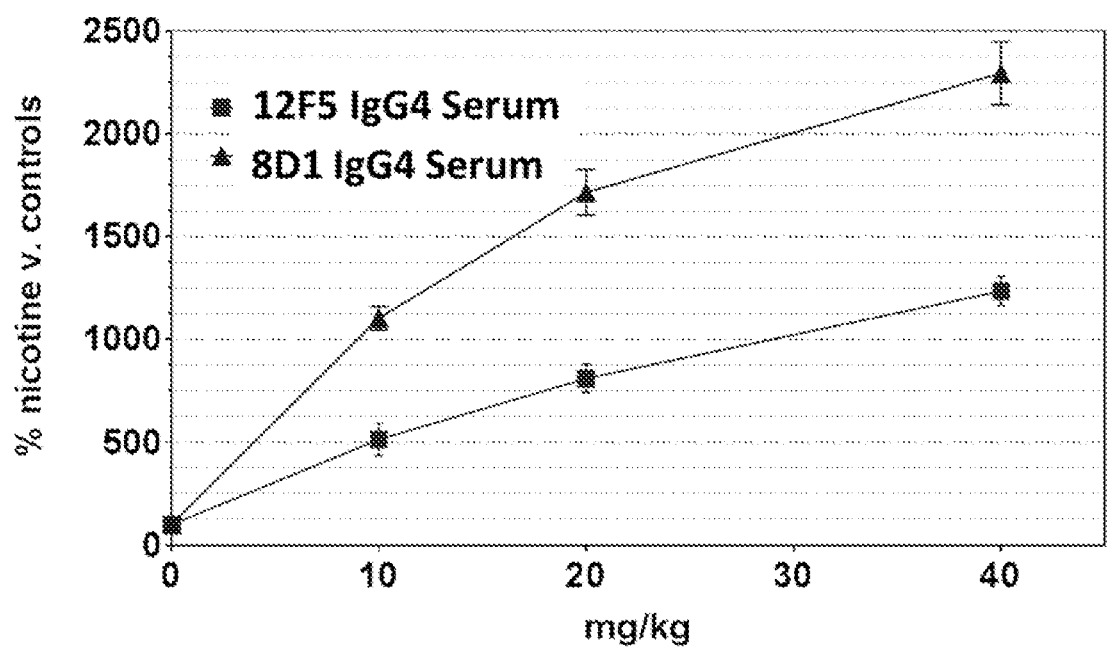
FIGS. 3A and 3B show the results from a dose response study of the exemplary nicotine-binding antibodies in rats.
Figure 3B:
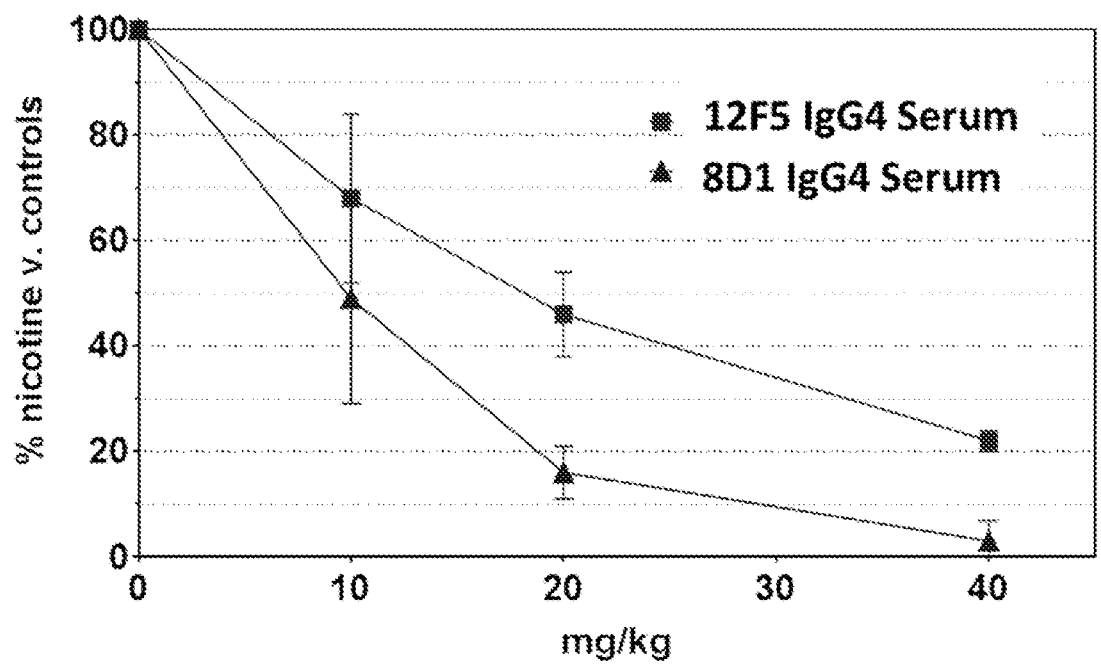

FIGS. 2A and 2B show the serum and brain concentrations, respectively. While both antibodies reduced the levels of nicotine in the brain, a 40 mg/kg dose of the 8D1 IgG4 antibody decreased the amount of nicotine localized in the brain by more than 95%. FIGS. 3A and 3B show the same data, but as a percentage of levels in control rats not pre-treated with antibody.

The 0.03 mg/kg dose of nicotine is equivalent to 2 cigarettes (mg/kg basis) and was administered as a rapid bolus (10s) in contrast to 5-10 minutes to smoke one cigarette. Serum levels of antibody were measured using ELISA and rats that had less than 5 µg/mL serum antibody level (due to incomplete administration) were excluded from the analyses. The excluded animals had an average serum antibody level of 0.73 µg/mL, while the rats included in the analysis had an average serum antibody level of 302 µg/mL. Compared to a control serum level of 21 ng/mL nicotine, single doses of 10, 20, and 40 mg/kg 8D1-IgG4 produced serum nicotine levels of 226, 351, and 470 ng/mL, corresponding respectively to 11-, 17-, and 22-fold of the control level (p=0.0057 by one-way ANOVA with Bonferroni correction for multiple comparisons). Compared to a control brain level of 139 ng/g nicotine, single doses of 10, 20, and 40 mg/kg 8D1-IgG4 produced brain nicotine levels of 68, 22, and 4 ng/g, corresponding respectively to 49%, 16%, and 3% of the control level (p=0.0045).

Example 5—Accelerated Stability Study

To determine the relative stability of exemplary nicotine-binding antibodies, antibodies 8D1-IgG4 and 12F5 IgG4 were formulated in phosphate buffer saline (PBS) at a concentration of approximately 10 mg/ml and incubated at 40° C. or 5° C. Samples were taken after 2 weeks and 4 weeks for analysis by Size Exclusion Chromatography and functional assay (direct binding to nicotine conjugate). The results of the stability studies are shown in Table 5 below.

TABLE 5

Stability of Exemplary Nicotine-Binding Antibodies

| Sample ID | Stability time point | Storage condition | Main Peak Area | % Aggregates | % Fragments |
|---|---|---|---|---|---|
| 12F5-IgG4 | 2 week | 5° C. | 461,532 | 0 | 0 |
|  |  | 40° C. | 523,855 | 1.2 | 0 |
|  | 4 week | 5° C. | 524,356 | 0 | 0 |
|  |  | 40° C. | 611,147 | 2.7 | 0 |
| 8D1-IgG4 | 2 week | 5° C. | 500,715 | 0.98 | 0 |
|  |  | 40° C. | 523,434 | 2.9 | 0 |
|  | 4 week | 5° C. | 476,309 | 0 | 0 |
|  |  | 40° C. | 586,613 | 4.0 | 0 |

Overall, stability of the nicotine-binding antibodies was acceptable, with a similar amount of monomer loss at week 4 for both antibodies that were tested. The functional (ELISA) assays showed identical functional binding to a nicotine-conjugate after 2 weeks storage.

Example 6—In Vivo Study of Acute Heavy Smoking

Figure 4A:
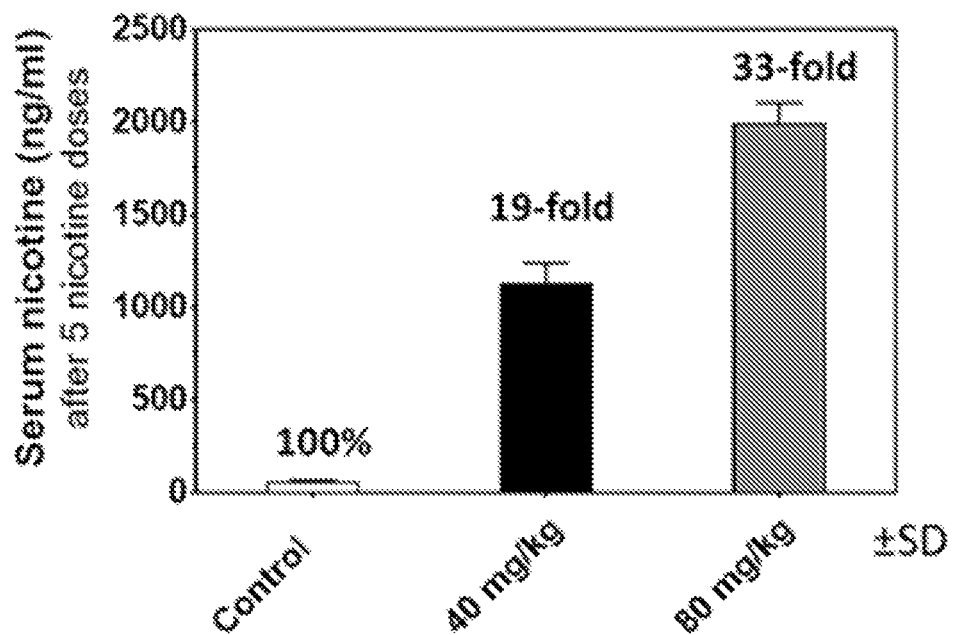
FIGS. 4A and 4B shows the impact of multiple doses of nicotine—simulating a heavy smoker—after pretreatment with disclosed nicotine-binding antibodies. When pretreated with 8D1-IgG4, rats showed an increase in serum nicotine levels after 5 nicotine doses (FIG. 4A) and a decrease in brain nicotine levels (FIG. 4B).
Figure 4B:
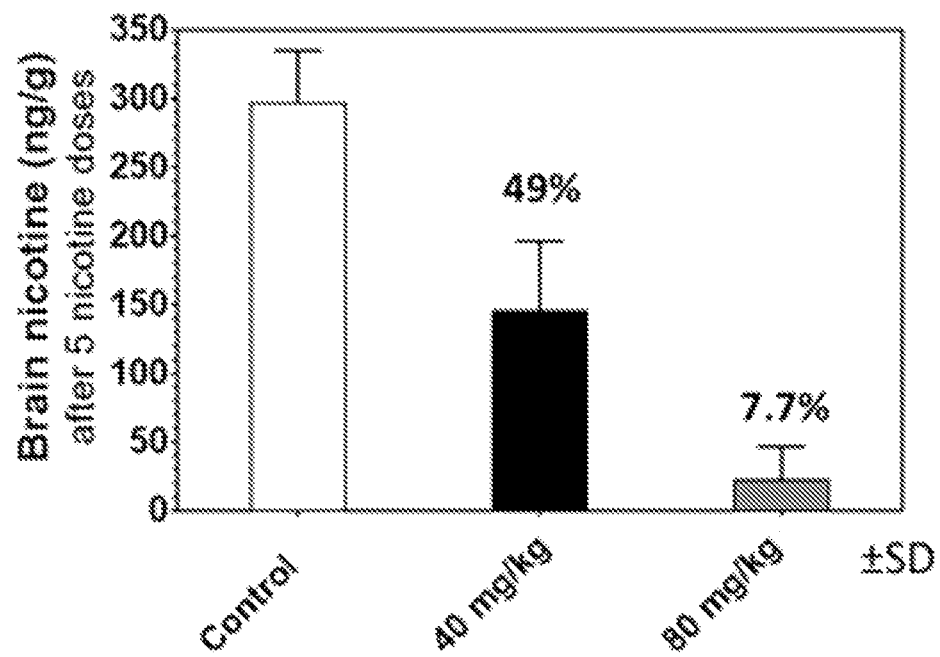

To test the effects of 8D1-IgG4 in a simulated scenario of acute heavy smoking, rats (N=10; 5 male and 5 female SD rats) pre-treated with 8D1-IgG4 or control IgG, received a series of 5 repeated intravenous nicotine doses spaced 10 minutes apart (FIG. 4). Total serum nicotine increased as a function of accumulated nicotine dosing, and in an 8D1-IgG4 dose-dependent manner (FIG. 4A). After the fifth nicotine dose, brain nicotine levels were reduced by more than 90% at the 80 mg/kg 8D1-IgG4 dose level, and by a more moderate 51% at the 40 mg/kg dose level, compared to control IgG (FIG. 4B). Compared to an average control serum level of 60 ng/mL nicotine following the $5^{th}$ nicotine dose, single doses of 40 and 80 mg/kg 8D1-IgG4 produced total serum nicotine levels of 1130 and 1987 ng/mL (<2% free nicotine, see below), corresponding respectively to 19 and 33-fold of the control level (p<0.0001 by one-way ANOVA with Bonferroni's correction). Compared to an average control brain level of 298 ng/g nicotine following the $5^{th}$ nicotine dose, single doses of 40 and 80 mg/kg 8D1-IgG4 produced brain levels of 146 and 23 ng/g, corresponding respectively to 49% and 8% of the control level (p=0.0006 by one-way ANOVA with Bonferroni's correction). These data indicate 8D1-IgG4 is well maintained at nicotine dosing rates simulating very heavy smoking (10 cigarettes over 40 minutes).

Example 7—In Vivo Study on Nicotine Self-Administration

Figure 5:
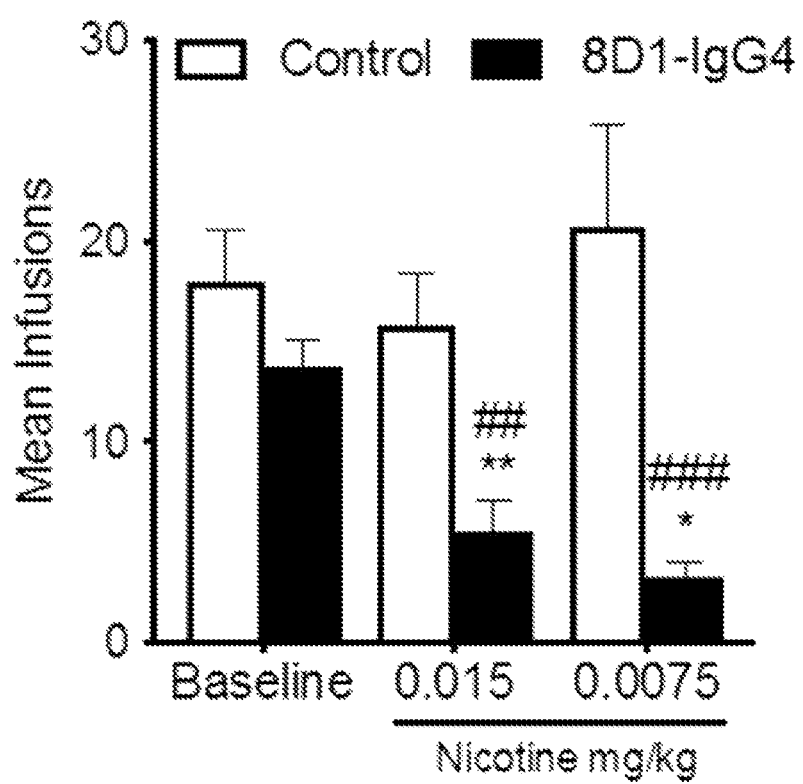
FIG. 5 shows that treatment with disclosed nicotine-binding antibodies reduces nicotine self-administration in rats. When rats were treated with 8D1-IgG4 the mean (±SEM) number of self-administered infusions during the last three sessions before (Baseline) was significantly higher than the number of infusions during antibody treatment at each unit nicotine dose.

To assess whether 8D1-IgG4 could reduce self-administration, rats were initially trained for nicotine self-administration (NSA) using a unit nicotine dose of 0.03 mg/kg under a fixed-ratio (FR) 3 schedule during 2 hour sessions. After stable NSA was established, the unit dose was reduced to 0.015 mg/kg, which results in serum nicotine concentrations more similar to smoking in humans. After NSA stabilized at this unit dose, rats received twice-weekly i.v. infusions of 160 mg/kg 8D1-IgG4 (N=7) or 160 mg/kg Gammagard (control mAb, N=7) 30 minutes prior to the session while rats continued NSA at the 0.015 mg/kg dose for 10 consecutive sessions. Then, the unit nicotine dose was reduced to 0.0075 mg/kg for another 10 consecutive sessions while mAb treatment continued. FIG. 5 shows the mean (±SEM) number of infusions during the last three sessions before (Baseline) and during mAb treatment at each unit nicotine dose. Rats given 8D1-IgG4 exhibited a significant decrease in NSA at both unit doses compared to their respective baseline and to control rats. These findings demonstrate that 8D1-IgG4 reduces the reinforcing effects of nicotine. Although the dose of 8D1-IgG4 was high, the effective dose for smoking cessation in humans will likely be much lower because people will be motivated to quit. As a point of reference, the potency of varenicline was considerably higher in clinical trials for smoking cessation than it was in preclinical nicotine self-administration studies in rats. Rollema, H. et al., *Neuropharmacology*, 52: 985-994 (2007).

Example 8—In Vivo Pharmacokinetic Studies

Figure 6:
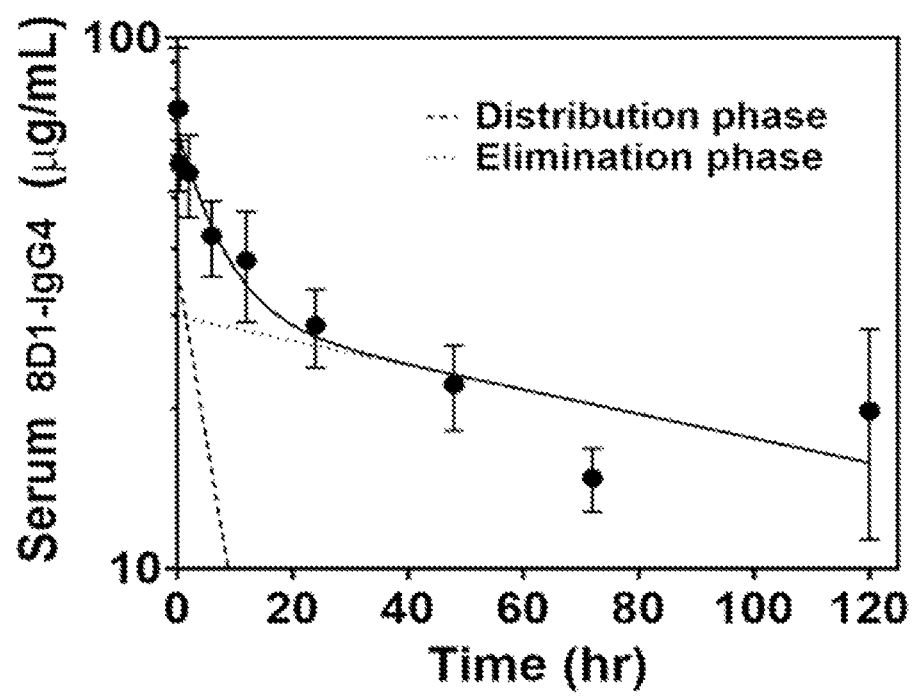
FIG. 6 shows the single dose pharmacokinetics of 8D1-IgG4 in rats when administered at a dose of 20 mg/kg.
Figure 7:
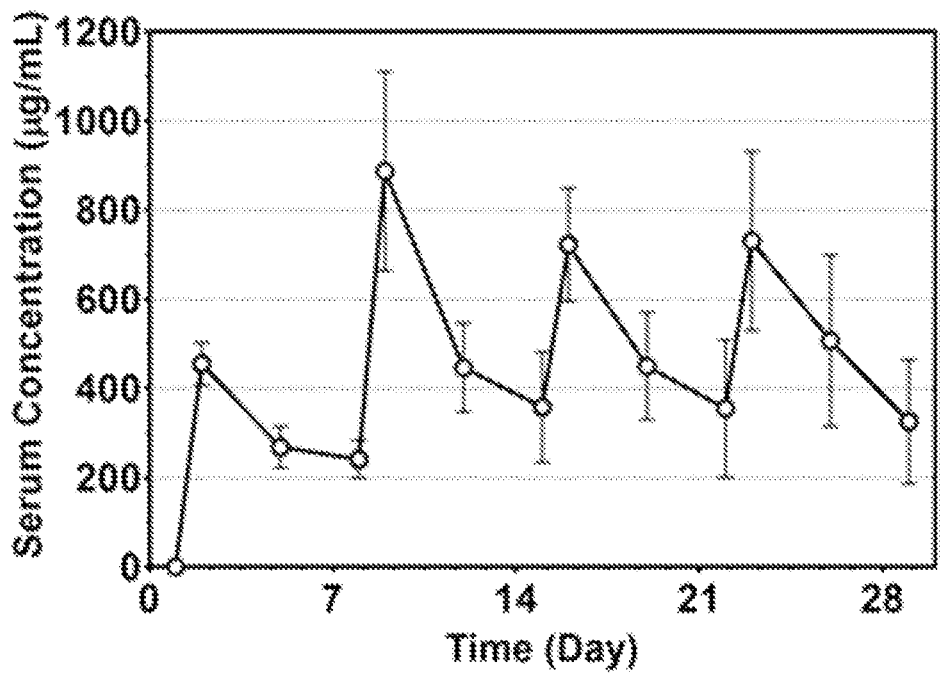
FIG. 7 shows the pharmacokinetics of repeated dosing of 8D1-IgG4 in rats over an extended period of time. Rats were administered a 40 mg/kg dose once per week for 4 weeks.

The pharmacokinetics of 8D1-IgG4 were tested in rats following a single dose (20 mg/kg; FIG. 6) and repeated doses (40 mg/kg; FIG. 7) of 8D1-IgG4 dosed weekly for 4 weeks in rats (N=6). Residual mAb concentrations were measured at various time points after i.v. dosing. The ELISA detection assay employed relies on binding to the nicotine conjugate 3' Am-S-(−)Nic-polyglutamic acid, and thus reflects functional mAb levels binding S-(−)-nicotine in serum. Parameters estimated by non-compartmental analysis of 8D1-IgG4 concentrations include an elimination phase half-life of 131 h, clearance of 0.10 mL/min/kg, and a steady-state $V_D$=79.2 mL/kg, respectively. Rodent PK assays of mAb's are not always predictive of PK in humans but are often used as a measure of "in vivo fitness" in the lead selection process. While not seen for 8D1-IgG4, an abnormally fast antibody clearance can be a sign of unwanted nonspecific interactions, so these assays are used to identify antibodies with high nonspecific disposition PK. At the end of this study, rats were dosed with 0.03 mg/kg i.v. nicotine and sacrificed 3 minutes later and samples were analyzed to assess the amount of unbound nicotine by before and after ultrafiltration. All samples had <2% unbound nicotine (data not shown).

Example 9—In Vivo Toxicity Study

To assess the toxicity of high doses of 8D1-IgG4, a non-GLP 4-week repeated, high-dose toxicology study of 8D1-IgG4 with and without concurrent administration of nicotine was conducted in rats to evaluate if any significant toxicity signals were observed. Four groups of 16 rats per group (8 male and 8 female) were tested: vehicle control, 8D1-IgG4 only, nicotine only, and 8D1-IgG4 plus nicotine—the latter to assess the safety of the nicotine:antibody complex. 8D1-IgG4 was dosed i.v. once weekly at 200 mg/kg. Nicotine was dosed continuously via infusion pump into the subcutaneous space (1 mg/kg/day for 28d).

Assessment of toxicity was based on mortality, clinical observations, and body weight during the course of the 28-day study, and at the end of study organ weights, gross anatomic pathology, hematology, serum clinical chemistry, and coagulation was performed. Histopathology of selected tissues (heart, liver, lung, kidney, spleen, skeletal muscle, brain, colon, stomach, ovary, and testis) is pending. Tissues were fixed immediately in formalin, and processed for embedding in paraffin, staining with H&E, and review by a veterinary pathologist.

8D1-IgG4 was well-tolerated with no obvious pathology in the treatment groups. All animals received the full dose and no mortality was induced in any animals. Daily clinical observations found no observable behavioral changes or modifications in feeding or grooming in any groups. Body weight was monitored twice weekly for the duration of the study and no significant differences between treatment groups was found. At the end of the study animals were necropsied and major organs (liver, lung, spleen, heart, kidneys, testis or ovaries) were isolated and weighed. No gross pathological findings were noted and no statistically significant changes in organ weights were found. Blood was collected, and complete blood count performed to determine any changes in hematological parameters. While occasional animals had values outside the normal range (e.g. slightly decreased lymphocytes or hemoglobin) no significant changes or trends were found in any group. There was a trend to have slight polychromasia in some of the animals that received nicotine. Serum clinical chemistry of 23 different analytes and plasma coagulation did not find any notable changes between treatment groups.

What is claimed is:

1. A nicotine-binding antibody or nicotine-binding fragment thereof, comprising the complementarity determining regions (CDRs) of a heavy chain sequence and a light chain sequence selected from;
   a. the heavy chain sequence of SEQ ID NO: 1 and the light chain sequence of SEQ ID NO: 2;
   b. the heavy chain sequence of SEQ ID NO: 3 and the light chain sequence of SEQ ID NO: 4;
   c. the heavy chain sequence of SEQ ID NO: 5 and the light chain sequence of SEQ ID NO: 6;
   d. the heavy chain sequence of SEQ ID NO: 7 and the light chain sequence of SEQ ID NO: 8;
   e. the heavy chain sequence of SEQ ID NO: 9 and the light chain sequence of SEQ ID NO: 10;
   f. the heavy chain sequence of SEQ ID NO: 11 and the light chain sequence of SEQ ID NO: 12;
   g. the heavy chain sequence of SEQ ID NO: 13 and the light chain sequence of SEQ ID NO: 14;
   h. the heavy chain sequence of SEQ ID NO: 15 and the light chain sequence of SEQ ID NO: 16;

i. the heavy chain sequence of SEQ ID NO: 17 and the light chain sequence of SEQ ID NO: 18;
j. the heavy chain sequence of SEQ ID NO: 19 and the light chain sequence of SEQ ID NO: 20.

2. The nicotine-binding antibody or nicotine-binding fragment thereof according to claim 1, further comprising the variable regions of the heavy chain sequence and the light chain sequence selected from:
   a. the heavy chain sequence of SEQ ID NO: 1 and the light chain sequence of SEQ ID NO: 2;
   b. the heavy chain sequence of SEQ ID NO: 3 and the light chain sequence of SEQ ID NO: 4;
   c. the heavy chain sequence of SEQ ID NO: 5 and the light chain sequence of SEQ ID NO: 6;
   d. the heavy chain sequence of SEQ ID NO: 7 and the light chain sequence of SEQ ID NO: 8;
   e. the heavy chain sequence of SEQ ID NO: 9 and the light chain sequence of SEQ ID NO: 10;
   f. the heavy chain sequence of SEQ ID NO: 11 and the light chain sequence of SEQ ID NO: 12;
   g. the heavy chain sequence of SEQ ID NO: 13 and the light chain sequence of SEQ ID NO: 14;
   h. the heavy chain sequence of SEQ ID NO: 15 and the light chain sequence of SEQ ID NO: 16;
   i. the heavy chain sequence of SEQ ID NO: 17 and the light chain sequence of SEQ ID NO: 18;
   j. the heavy chain sequence of SEQ ID NO: 19 and the light chain sequence of SEQ ID NO: 20.

3. The nicotine-binding antibody or nicotine-binding fragment thereof according to claim 1, comprising the heavy chain sequence and the light chain sequence of:
   a. the heavy chain sequence of SEQ ID NO: 1 and the light chain sequence of SEQ ID NO: 2;
   b. the heavy chain sequence of SEQ ID NO: 3 and the light chain sequence of SEQ ID NO: 4;
   c. the heavy chain sequence of SEQ ID NO: 5 and the light chain sequence of SEQ ID NO: 6;
   d. the heavy chain sequence of SEQ ID NO: 7 and the light chain sequence of SEQ ID NO: 8;
   e. the heavy chain sequence of SEQ ID NO: 9 and the light chain sequence of SEQ ID NO: 10;
   f. the heavy chain sequence of SEQ ID NO: 11 and the light chain sequence of SEQ ID NO: 12;
   g. the heavy chain sequence of SEQ ID NO: 13 and the light chain sequence of SEQ ID NO: 14;
   h. the heavy chain sequence of SEQ ID NO: 15 and the light chain sequence of SEQ ID NO: 16;
   i. the heavy chain sequence of SEQ ID NO: 17 and the light chain sequence of SEQ ID NO: 18;
   j. the heavy chain sequence of SEQ ID NO: 19 and the light chain sequence of SEQ ID NO: 20;
   k. the heavy chain sequence of SEQ ID NO: 21 and the light chain sequence of SEQ ID NO: 22;
   l. the heavy chain sequence of SEQ ID NO: 23 and the light chain sequence of SEQ ID NO: 24;
   m. the heavy chain sequence of SEQ ID NO: 25 and the light chain sequence of SEQ ID NO: 26;
   n. the heavy chain sequence of SEQ ID NO: 27 and the light chain sequence of SEQ ID NO: 28;
   o. the heavy chain sequence of SEQ ID NO: 29 and the light chain sequence of SEQ ID NO: 30;
   p. the heavy chain sequence of SEQ ID NO: 31 and the light chain sequence of SEQ ID NO: 32;
   q. the heavy chain sequence of SEQ ID NO: 33 and the light chain sequence of SEQ ID NO: 34;
   r. the heavy chain sequence of SEQ ID NO: 35 and the light chain sequence of SEQ ID NO: 36;
   s. the heavy chain sequence of SEQ ID NO: 37 and the light chain sequence of SEQ ID NO: 38; or
   t. the heavy chain sequence of SEQ ID NO: 39 and the light chain sequence of SEQ ID NO: 40.

4. The antibody of claim 3, comprising two heavy chains comprising SEQ ID NO: 27 and two light chains comprising SEQ ID NO: 28.

5. The antibody of claim 4 consisting of two heavy chains comprising SEQ ID NO: 27 and two light chains comprising SEQ ID NO: 28.

6. A pharmaceutical composition comprising the nicotine-binding antibody of claim 4, and a pharmaceutically acceptable carrier, wherein the composition is formulated for injection or infusion.

7. A method of treating nicotine addiction or facilitating smoking cessation comprising administering to a human subject in need thereof a therapeutically effective amount of the antibody of claim 4.

8. A method of treating nicotine overdose or nicotine poisoning comprising administering to a human subject in need thereof a therapeutically effective amount of the antibody of claim 4.

9. The nicotine-binding antibody or nicotine-binding fragment thereof according to claim 1, wherein the antibody or fragment is an IgG4.

10. The nicotine-binding antibody or nicotine-binding fragment thereof according to claim 1, wherein the antibody or fragment comprises the substitution S228P.

11. The nicotine-binding antibody or nicotine-binding fragment thereof according to claim 1, wherein the antibody or fragment is a long-acting variant.

12. The nicotine-binding antibody or nicotine-binding fragment thereof according to claim 11, wherein the antibody or fragment is PEGylated.

13. The nicotine-binding antibody or nicotine-binding fragment thereof according to claim 1, wherein the antibody or fragment has a $K_D$ for S-(−)-nicotine of less than about 100 nM.

14. The nicotine-binding antibody or nicotine-binding fragment thereof according to claim 1, wherein the antibody or fragment is substantially not cross-reactive with one or more nicotine-related compounds selected from cotinine, nicotinamide, B-nicotinamide adenine dinucleotide and nornicotine.

15. A pharmaceutical composition comprising a nicotine-binding antibody or nicotine-binding fragment thereof according to claim 1 and a pharmaceutically acceptable carrier.

16. The pharmaceutical composition according to claim 15, wherein the composition is formulated for injection or infusion.

17. A method of treating nicotine addiction or facilitating smoking cessation, comprising administering to a human subject in need thereof a therapeutically effective amount of a nicotine-binding antibody or nicotine-binding fragment thereof according to claim 1.

18. A method of treating nicotine overdose or nicotine poisoning, comprising administering to a mammalian subject in need thereof a therapeutically effective amount of a nicotine-binding antibody or nicotine-binding fragment thereof according to claim 1.

* * * * *